(12) United States Patent
Viens et al.

(10) Patent No.: US 12,138,146 B2
(45) Date of Patent: *Nov. 12, 2024

(54) FLUID MANAGEMENT LAYER FOR AN ABSORBENT ARTICLE

(71) Applicant: The Procter & Gamble Company, Cincinnati, OH (US)

(72) Inventors: Gerard A. Viens, Wyoming, OH (US); Carlos Domingo Naranjo Martin, Frankfurt (DE); Paul Dominic Mellor, Kelkheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 785 days.

This patent is subject to a terminal disclaimer.

(21) Appl. No.: 16/831,862

(22) Filed: Mar. 27, 2020

(65) Prior Publication Data
US 2020/0315870 A1 Oct. 8, 2020

Related U.S. Application Data

(60) Provisional application No. 62/946,738, filed on Dec. 11, 2019, provisional application No. 62/946,725,
(Continued)

(51) Int. Cl.
*A61F 13/15* (2006.01)
*A61F 13/511* (2006.01)
(Continued)

(52) U.S. Cl.
CPC ...... *A61F 13/535* (2013.01); *A61F 13/15203* (2013.01); *A61F 13/15747* (2013.01);
(Continued)

(58) Field of Classification Search
CPC .............. A61F 13/535; A61F 13/15203; A61F 13/15747; A61F 13/1511; A61F 13/511;
(Continued)

(56) References Cited

U.S. PATENT DOCUMENTS

| 3,156,242 A | 11/1964 | Crowe, Jr. |
| 3,881,489 A | 5/1975 | Hartwell |

(Continued)

FOREIGN PATENT DOCUMENTS

| CN | 101677889 A | 3/2010 |
| CN | 103429207 A | 12/2013 |

(Continued)

OTHER PUBLICATIONS

International Search Report and Written Opinion; Application Ser. No. PCT/US2020/025127; dated Aug. 3, 2020; 15 pages.
(Continued)

*Primary Examiner* — Jacqueline F Stephens
(74) *Attorney, Agent, or Firm* — Sarah M. DeCristofaro; George Leal

(57) ABSTRACT

A fluid management layer having an integrated, carded, nonwoven is described. The fluid management layer has a basis weight of between about 40 grams per square meter (gsm) and about 75 gsm; a plurality of absorbent fibers, a plurality of stiffening fibers and a plurality of resilient fibers; wherein the fluid management layer exhibits a total compression of greater than 0.40 mm and has a total recovery of at least 0.35 mm, and wherein the fluid management layer has a density of less than or equal to 0.08 g/cc.

20 Claims, 7 Drawing Sheets

Related U.S. Application Data filed on Dec. 11, 2019, provisional application No. 62/829,280, filed on Apr. 4, 2019.

(51) Int. Cl.

| | | |
|---|---|---|
| *A61F 13/512* | (2006.01) | |
| *A61F 13/513* | (2006.01) | |
| *A61F 13/514* | (2006.01) | |
| *A61F 13/53* | (2006.01) | |
| *A61F 13/534* | (2006.01) | |
| *A61F 13/535* | (2006.01) | |
| *A61F 13/537* | (2006.01) | |
| A61F 13/47 | (2006.01) | |
| A61F 13/84 | (2006.01) | |

(52) U.S. Cl.
CPC .......... *A61F 13/511* (2013.01); *A61F 13/512* (2013.01); *A61F 13/513* (2013.01); *A61F 13/514* (2013.01); *A61F 13/53* (2013.01); *A61F 13/534* (2013.01); *A61F 13/53708* (2013.01); *A61F 13/5376* (2013.01); *A61F 2013/15292* (2013.01); *A61F 2013/15325* (2013.01); *A61F 2013/15357* (2013.01); *A61F 2013/15373* (2013.01); *A61F 2013/15406* (2013.01); *A61F 2013/15422* (2013.01); *A61F 2013/15447* (2013.01); *A61F 2013/15959* (2013.01); *A61F 2013/4708* (2013.01); *A61F 2013/51169* (2013.01); *A61F 2013/51178* (2013.01); *A61F 2013/530233* (2013.01); *A61F 2013/53024* (2013.01); *A61F 2013/530452* (2013.01); *A61F 2013/53062* (2013.01); *A61F 2013/53791* (2013.01); *A61F 2013/8402* (2013.01)

(58) Field of Classification Search
CPC .... A61F 13/512; A61F 13/513; A61F 13/514; A61F 13/534; A61F 2013/15292; A61F 2013/15325; A61F 2013/15357; A61F 2013/15373; A61F 2013/15406; A61F 2013/15422; A61F 2013/15959; A61F 2013/4708; A61F 2013/1169; A61F 2013/1178; A61F 2013/530233; A61F 2013/53024; A61F 2013/530452; A61F 2013/53062; A61F 2013/53791; A61F 2013/8402

See application file for complete search history.

(56) References Cited

U.S. PATENT DOCUMENTS

| | | | |
|---|---|---|---|
| 3,989,867 A | 11/1976 | Sisson | |
| 4,341,216 A | 7/1982 | Obenour | |
| 4,591,523 A | 5/1986 | Thompson | |
| 4,695,422 A | 9/1987 | Curro et al. | |
| 4,713,068 A | 12/1987 | Wang et al. | |
| 4,818,600 A | 4/1989 | Braun et al. | |
| 4,839,216 A | 6/1989 | Curro et al. | |
| 5,433,715 A | 7/1995 | Tanzer | |
| 5,458,835 A | 10/1995 | Wilkes et al. | |
| 5,599,335 A | 2/1997 | Goldman | |
| 5,607,414 A | 3/1997 | Richards | |
| 5,634,914 A | 6/1997 | Wilkes et al. | |
| 5,810,796 A | 9/1998 | Kimura | |
| 5,885,265 A | 3/1999 | Osborn, III et al. | |
| 5,997,980 A | 12/1999 | Matoba | |
| 6,060,638 A | 5/2000 | Paul | |
| 6,333,108 B1 | 12/2001 | Wilkes et al. | |
| 6,436,508 B1 | 8/2002 | Ciammaichella et al. | |
| 6,462,251 B1 | 10/2002 | Cimini et al. | |
| 6,547,018 B1 | 4/2003 | Choi | |
| 6,623,464 B2 | 9/2003 | Bewick-sonntag | |
| 6,624,341 B1 | 9/2003 | Depner et al. | |
| 6,642,432 B1 | 11/2003 | Matsui et al. | |
| 6,664,439 B1 | 12/2003 | Arndt et al. | |
| 6,838,154 B1 | 1/2005 | Varona et al. | |
| 6,989,005 B1 | 1/2006 | Lavon et al. | |
| 7,597,689 B2 | 10/2009 | Hoffmann | |
| 7,686,790 B2 | 3/2010 | Rasmussen et al. | |
| 7,750,203 B2 | 7/2010 | Becker et al. | |
| 7,767,598 B2 | 8/2010 | Schneider et al. | |
| 8,389,427 B2 | 3/2013 | Gustafsson | |
| 8,466,336 B2 | 6/2013 | Carlucci et al. | |
| 9,295,593 B2 | 3/2016 | Van Malderen | |
| 9,693,910 B2 | 7/2017 | Carlucci et al. | |
| 9,789,009 B2 | 10/2017 | Joseph | |
| 10,307,309 B2 | 6/2019 | Viens et al. | |
| 10,532,123 B2 | 1/2020 | Viens | |
| 11,285,055 B2 | 3/2022 | Viens et al. | |
| 2001/0027303 A1 | 10/2001 | Bewick-sonntag | |
| 2002/0101191 A1 | 8/2002 | Dolan et al. | |
| 2003/0050615 A1 | 3/2003 | Sakamoto et al. | |
| 2003/0220048 A1 | 11/2003 | Toro | |
| 2004/0018795 A1 | 1/2004 | Viazmensky | |
| 2004/0087924 A1 | 5/2004 | Sroda | |
| 2004/0238393 A1 | 12/2004 | Ohi et al. | |
| 2005/0015068 A1 | 1/2005 | Bean et al. | |
| 2005/0033253 A1 | 2/2005 | Fuchs | |
| 2005/0136773 A1 | 6/2005 | Yahiaoui | |
| 2006/0058762 A1 | 3/2006 | Yang | |
| 2008/0113574 A1 | 5/2008 | Neron | |
| 2008/0119806 A1 | 5/2008 | Nguyen | |
| 2008/0312622 A1 | 12/2008 | Hundorf | |
| 2011/0060303 A1 | 3/2011 | Bissah et al. | |
| 2011/0282309 A1 | 11/2011 | Adie et al. | |
| 2012/0029460 A1 | 2/2012 | Yamashita et al. | |
| 2012/0041410 A1 | 2/2012 | Ueda | |
| 2014/0005622 A1 | 1/2014 | Wirtz | |
| 2014/0343523 A1* | 11/2014 | Viens .................... A61L 15/225 162/146 |
| 2015/0182387 A1 | 7/2015 | Ferrer et al. | |
| 2015/0250654 A1 | 9/2015 | Pernot | |
| 2015/0351976 A1 | 12/2015 | Viens | |
| 2016/0213532 A1 | 7/2016 | Takahashi | |
| 2017/0119597 A1 | 5/2017 | Bewick-sonntag | |
| 2017/0312148 A1 | 11/2017 | Dobrosielska-oura et al. | |
| 2018/0098889 A1 | 4/2018 | Hardie | |
| 2018/0098893 A1 | 4/2018 | Viens | |
| 2018/0133071 A1 | 5/2018 | Miao et al. | |
| 2019/0099301 A1 | 4/2019 | Viens et al. | |
| 2019/0247244 A1 | 8/2019 | Viens | |
| 2020/0101191 A1 | 4/2020 | Viens | |
| 2020/0315859 A1 | 10/2020 | Denti et al. | |
| 2020/0315861 A1 | 10/2020 | Viens | |
| 2020/0315871 A1 | 10/2020 | Viens et al. | |
| 2020/0315872 A1 | 10/2020 | Viens et al. | |
| 2020/0315873 A1 | 10/2020 | Viens et al. | |
| 2020/0315874 A1 | 10/2020 | Viens et al. | |
| 2023/0329922 A1 | 10/2023 | Viens et al. | |

FOREIGN PATENT DOCUMENTS

| | | |
|---|---|---|
| CN | 103429209 A | 12/2013 |
| CN | 103874472 A | 6/2014 |
| CN | 105208991 A | 12/2015 |
| CN | 106460268 A | 2/2017 |
| EP | 0710472 B1 | 4/2001 |
| EP | 1504739 A1 | 2/2005 |
| EP | 2407133 A1 | 1/2012 |
| EP | 2450012 A1 | 5/2012 |
| EP | 2692321 | 2/2014 |
| EP | 2740454 A1 | 6/2014 |
| JP | H06136650 A | 5/1994 |
| JP | H10273884 | 10/1998 |
| JP | 2003024371 A | 1/2003 |
| JP | 2007500047 A | 1/2007 |
| JP | 2008106383 A | 5/2008 |
| JP | 2014512864 A | 5/2014 |
| JP | 2017516924 A | 6/2017 |
| WO | 9110416 A1 | 7/1991 |

(56) References Cited

FOREIGN PATENT DOCUMENTS

| | | |
|---|---:|---:|
| WO | 9724097 A1 | 7/1997 |
| WO | WO9723182 A1 | 7/1997 |
| WO | 0034085 A1 | 6/2000 |
| WO | 0059431 A1 | 10/2000 |
| WO | WO0134085 A1 | 5/2001 |
| WO | 0134215 A3 | 12/2001 |
| WO | 2007014235 A1 | 2/2007 |
| WO | WO2008066417 A1 | 6/2008 |
| WO | 2018197937 A1 | 11/2018 |
| WO | 2020205946 A1 | 10/2020 |

OTHER PUBLICATIONS

All Office Actions for U.S. Appl. No. 14/278,481, filed May 15, 2014.
All Office Actions for U.S. Appl. No. 16/701,547, filed Dec. 3, 2019.
All Office Actions; U.S. Appl. No. 16/831,879, filed Mar. 27, 2020.
All Office Actions; U.S. Appl. No. 16/831,865, filed Mar. 27, 2020.
All Office Actions; U.S. Appl. No. 16/831,868, filed Mar. 27, 2020.
All Office Actions; U.S. Appl. No. 16/831,870, filed Mar. 27, 2020.

\* cited by examiner

FLUID MANAGEMENT LAYER FOR AN ABSORBENT ARTICLE

TECHNICAL FIELD

The present disclosure generally relates to fluid management layer for a disposable absorbent article, in particular, a fluid management layer that is a carded, staple-fiber, nonwovens having improved performance characteristics.

BACKGROUND

Disposable absorbent articles such as feminine hygiene products, taped diapers, pant-type diapers and incontinence products are designed to absorb fluids from the wearer's body. Users of such disposable absorbent articles have several concerns. For example, leakage from products like catamenial pads, diapers, sanitary napkins, and incontinence pads is a significant concern. Additionally, comfort and the feel of the product against the wearer's body is also a concern. To provide better comfort, current disposable absorbent articles are typically provided with a topsheet that is flexible, soft feeling, and non-irritating to the wearer's skin. The topsheet does not itself hold the discharged fluid. Instead, the topsheet is fluid-permeable to allow the fluids to flow into an absorbent core.

Regarding comfort, some consumers may desire a product that has sufficient thickness and stiffness to provide the desirable amount of protection while also being flexible. Lofty materials may be utilized to provide a thick cushiony feeling article. However, in use these lofty materials can experience various compressive loads. Recovery from these compressive loads is paramount in maintaining the cushiony feeling of the article. Exacerbating this issue is the fact that the characteristics of the materials of the absorbent article change once fluid is introduced into the article. Hence, an article that may meet a consumer's requisite criteria before use may no longer be comfortable, flexible, or have the desired stiffness to the user after a given amount of fluid has been absorbed by the absorbent article.

As such there is a need to create fluid management materials that have sufficient caliper and compressive recovery for use in absorbent articles.

SUMMARY

Absorbent articles of the present disclosure comprise a topsheet, a backsheet, and an absorbent core disposed between the topsheet and the backsheet. A fluid management layer is disposed between the topsheet and the absorbent core. The fluid management layer comprises a carded, staple-fiber nonwoven material comprising a plurality of fibers.

A fluid management layer of the present disclosure has a basis weight of between about 40 grams per square meter (gsm) and about 75 gsm, the fluid management layer comprising a plurality of absorbent fibers, a plurality of stiffening fibers and a plurality of resilient fibers, wherein the fluid management layer exhibits a total compression of greater than 0.40 mm and has a total recovery of at least 0.35 mm, and wherein the fluid management layer has a density of less than or equal to 0.08 g/cc. In another execution, a fluid management layer of the present disclosure comprises a plurality of absorbent fibers, a plurality of stiffening fibers, and a plurality of resilient fibers. The fluid management layer can have a ratio of absorbent fibers in the fluid management layers of the present disclosure to stiffening fibers by weight percentage is less than 1:1, less than 0.6:1, or less than 0.5:1, specifically reciting all values within these ranges and any ranges created thereby. Similarly, a ratio of absorbent fibers in the fluid management layers of the present disclosure to resilient fibers by weight percentage is less than 1:1, less than 0.8:1, or less than 0.7:1, specifically reciting all values within these ranges and any ranges created thereby.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION

Figure 1A:
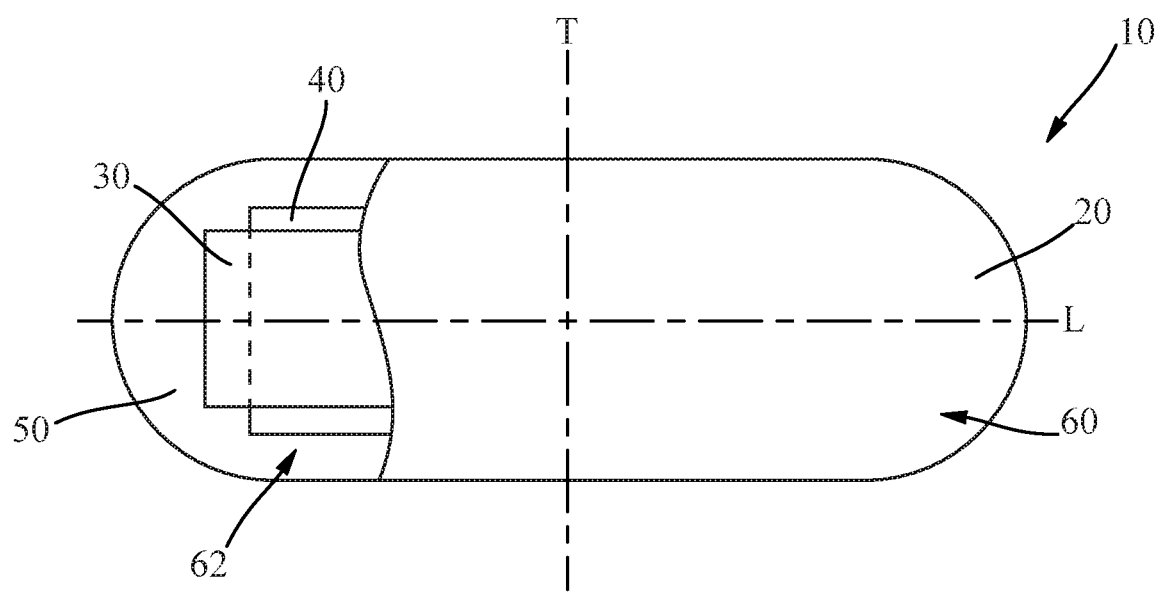
FIG. 1A is a schematic representation of a disposable absorbent article constructed in accordance with the present disclosure.

As used herein, the following terms shall have the meaning specified thereafter:

"Absorbent article" refers to wearable devices, which absorb and/or contain liquid, and more specifically, refers to devices, which are placed against or in proximity to the body of the wearer to absorb and contain the various exudates discharged from the body. Absorbent articles can include diapers, training pants, adult incontinence undergarments (e.g., liners, pads and briefs) and/or feminine hygiene products.

The "longitudinal" direction is a direction running parallel to the maximum linear dimension, typically the longitudinal axis, of the article and includes directions within 45° of the longitudinal direction. "Length" of the article or component thereof, when used herein, generally refers to the size/distance of the maximum linear dimension, or typically to the size/distance of the longitudinal axis, of an article or part thereof.

The "lateral" or "transverse" direction is orthogonal to the longitudinal direction, i.e. in the same plane of the majority of the article and the longitudinal axis, and the transverse direction is parallel to the transverse axis. "Width" of the article or of a component thereof, when used herein, refers to the size/distance of the dimension orthogonal to the longitudinal direction of the article or component thereof, i.e. orthogonal to the length of the article or component thereof, and typically it refers to the distance/size of the dimension parallel of the transverse axis of the article or component.

The "Z-direction" is orthogonal to both the longitudinal and transverse directions.

"Machine Direction" or "MD" as used herein means the direction parallel to the flow of the carded staple-fiber nonwoven through the nonwoven making machine and/or absorbent article product manufacturing equipment.

"Cross Machine Direction" or "CD" as used herein means the direction parallel to the width of the carded staple-fiber nonwoven making machine and/or absorbent article product manufacturing equipment and perpendicular to the machine direction.

The term "integrated" as used herein is used to describe fibers of a nonwoven material which have been intertwined, entangled, and/or pushed/pulled in a positive and/or negative Z-direction (direction of the thickness of the nonwoven material). Some exemplary processes for integrating fibers of a nonwoven web include spunlacing and needlepunching. Spunlacing uses a plurality of high-pressure water jets to entangle fibers. Needlepunching involves the use of needles to push and/or pull fibers to entangle them with other fibers in the nonwoven. And this type of integration obviates the need for adhesive or a binding agent to hold the fibers of the fluid management layer together.

The term "carded" as used herein is used to describe structural features of the fluid management layers described herein. A carded nonwoven utilizes fibers which are cut to a specific length, otherwise known as "staple length fibers." Staple length fibers may be any suitable length. For example, staple length fibers may have a length of up to 120 mm or may have a length as short as 10 mm. However, if a particular group of fibers are staple length fibers, for example viscose fibers, then the length of each of the viscose fibers in the carded nonwoven is predominantly the same, i.e. the staple length. It is worth noting that where additional staple fiber length fiber types are included, for example, polypropylene fibers, the length of each of the polypropylene fibers in the carded nonwoven is also predominantly the same. But, the staple length of the viscose and the staple length of the polypropylene may be different.

In contrast, continuous filaments such as by spunbonding or meltblowing processes, do not create staple length fibers. Instead, these filaments are of an indeterminate length and are not cut to a specific length as noted regarding their staple fiber length counterparts.

A carded, integrated, nonwoven as disclosed herein can be used in a variety of disposable absorbent articles, but is particularly useful in diapers, feminine hygiene products and incontinence products such as sanitary napkins and incontinence pads. The integrated, carded, nonwovens of the present disclosure can be particularly effective as a fluid management layer in the above absorbent articles. Additionally, the carded, integrated, nonwoven of the present disclosure provides increased caliper, even at lower basis weights, has good compressions recovery characteristics, and can provide a stain masking benefit.

A schematic cross-section of an exemplary absorbent article is shown in FIG. 1A. As shown, absorbent articles 10 in accordance with the present disclosure comprise a topsheet 20, a backsheet 50, and an absorbent core 40 disposed between the topsheet 20 and the backsheet 50. A fluid management layer 30 is disposed between the topsheet 20 and the absorbent core 40. The absorbent article has a wearer-facing surface 60 and an opposing garment-facing surface 62. The wearer-facing surface 60 primarily comprises the topsheet 20 while the garment-facing surface 62 primarily comprises the backsheet 50. Additional components may be included in either the wearer-facing surface 60 and/or the garment-facing surface 62. For example, where the absorbent article is an incontinent pad, a pair of barrier cuffs which extend generally parallel to a longitudinal axis L of the absorbent article 10, may also form a portion of the wearer-facing surface 60. Similarly, a fastening adhesive may be present on the backsheet 50 and form a portion of the garment-facing surface 62 of the absorbent article.

Figure 1B:
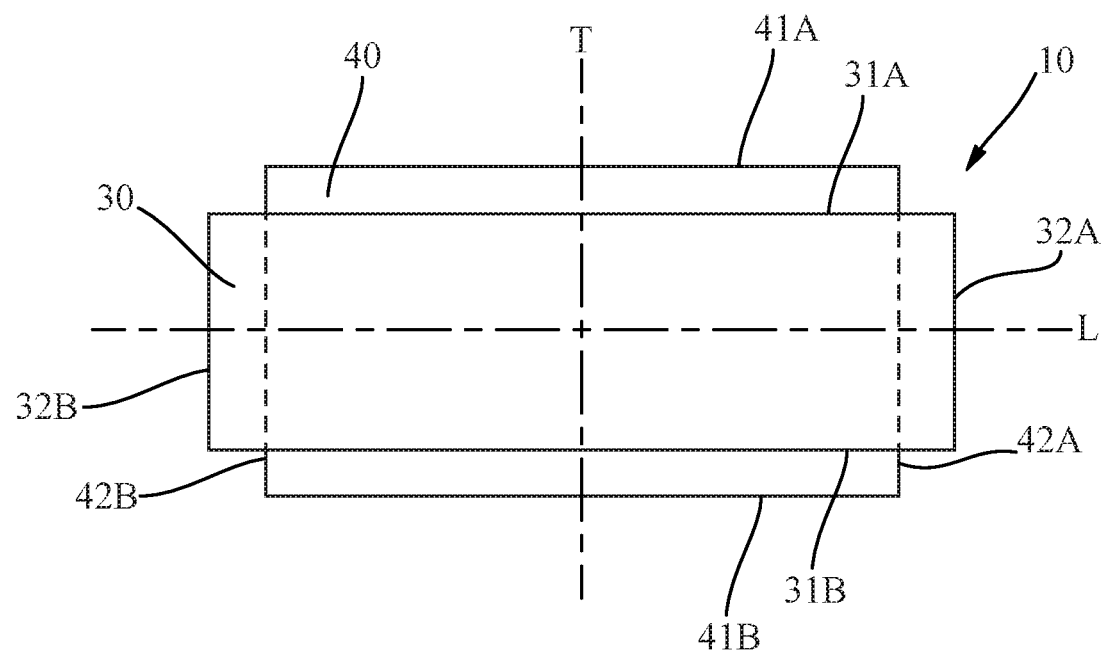
FIG. 1B is a schematic representation of an absorbent system of the disposable absorbent article shown in FIG. 1A.

Referring now to FIGS. 1A and 1B, the fluid management layer 30 comprises opposing end edges 32A and 32B which may extend generally parallel to a transverse axis T. And, the fluid management layer 30 comprises side edges 31A and 32B which may extend generally parallel to the longitudinal axis L. Similarly, the absorbent core 40 comprises opposing end edges 42A and 42B which may extend generally parallel to the transverse axis T. And, the absorbent core 40 may comprise side edges 41A and 41B which extend generally parallel to the longitudinal axis L.

As shown, each of the end edges 32A and 32B of the fluid management layer 30 may be disposed longitudinally outboard of the absorbent core 40. However, this is not necessarily required. For example, the end edges 32A and/or 32B may be coextensive with the absorbent core 40 or the end edges 32A and/or 32B may be disposed longitudinally inboard of the end edges 42A and/or 42B of the absorbent core 40.

Similarly, the side edges 31A and/or 31B may be disposed transversely outboard of the side edges 41A and/or 41B of the absorbent core 40. Or, the side edges 31A and/or 31B may be coextensive with the side edges 41A and/or 41B of the absorbent core 40.

As noted previously, the fluid management layers of the present disclosure are integrated, carded, nonwoven materials. A wide variety of configurations for a fluid management layer may be achieved. However, it is important that the fluid management layer of the present disclosure have adequate openness to allow for quick acquisition of fluid yet also be able to lock away liquid insults to reduce the likelihood of rewet. The fluid management layers of the present disclosure may comprise a plurality of carded webs. With this in mind, the carded webs which make up the fluid management layer may be different from one another. For example, one of the carded webs may comprise a different fiber blend than the others. Specifically, assuming the first carded web would be closest to the wearer-facing surface in an absorbent article, the fiber selection for a first carded web may be such that there is more openness associated with this web. A second carded web may be similarly configured. In contrast, a third carded web may be configured to collect liquid insults from the void space of the first and second carded webs and effectively distribute these liquid insults to an absorbent core (heterogeneous configuration). Alternatively, the first carded web, the second carded web and the third carded web may be configured the same, e.g. have the same fiber blend (homogeneous configuration).

Figure 2:
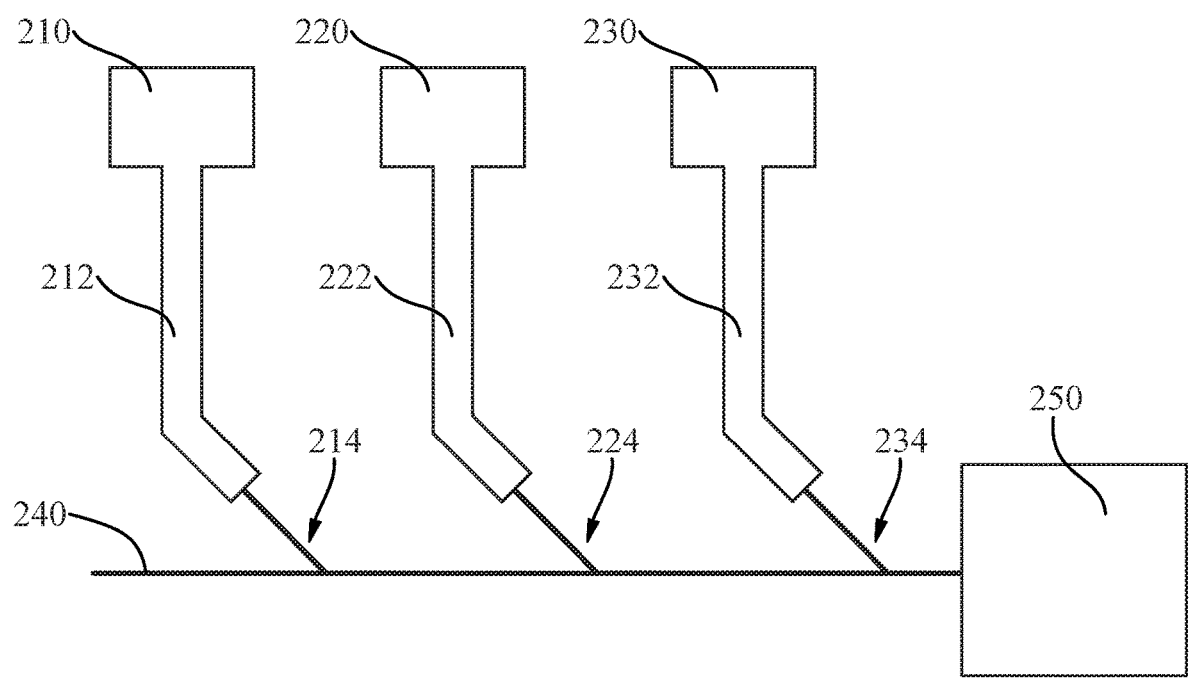
FIG. 2 is a schematic representation of a process which can be utilized to construct fluid management layer of the present disclosure.

A schematic representation of an exemplary carding and integrating process suitable for creating the fluid management layer 30 of the present disclosure is provided in FIG. 2. As shown, a plurality of carding machines 210, 220, and 230 may each create a carded nonwoven web, e.g. 214, 224, and 234, respectively, which is transferred to a carrier belt 240. Each of the carded nonwoven webs 214, 224, and 234, may be provided to the carrier belt 240 via a web chute 212, 222, 232, respectively. It is also worth noting that after the carded nonwoven 214 is deposited on the carrier belt 240, the carded nonwoven 224 is then deposited on the first carded nonwoven 214 on the carrier belt 240. Similarly, the third carded nonwoven web 234 deposited on the second carded nonwoven 224 and the first carded nonwoven 214 on the carrier belt 240. Subsequently, each of the first, second, and third carded nonwoven webs 214, 224, and 234 are then provided to an integration process 250 which utilizes either needles and/or high-pressure water streams to entangle the fibers of the first, second, and third carded nonwoven webs. Both carding and integration processes are well known in the art. As noted, the fluid management layers of the present disclosure comprise one or more carded webs. In instances where the fluid management layer comprises two carded webs, the need for a third carding machine may be obviated. Additional carding machines may be utilized. The resultant structure would be a nonwoven web with four strata.

It is worth noting that the fluid management layer of the present disclosure (particularly those where the strata are homogeneous, only one carding machine may be required. However, such operation may be inefficient as the one card would be required to deposit the requisite basis weight of fibers.

Once the carded web(s) are integrated, they cannot be manually separated—at least not without substantial effort and time. Each carded nonwoven web forms a stratum in the overall fluid management layer. Each stratum can maintain its unique properties for at least a portion of the stratum along the z-direction, even when integrated into a larger fluid management layer. The fluid management layer provides capillary suction to "pull" fluid through the topsheet, which is competing for trickle/low flow conditions. The fluid management layer also can contain a gush by providing distribution functions to efficiently utilize the absorbent core, as well as provide intermediate storage until the absorbent core can accept fluid.

Figure 3:
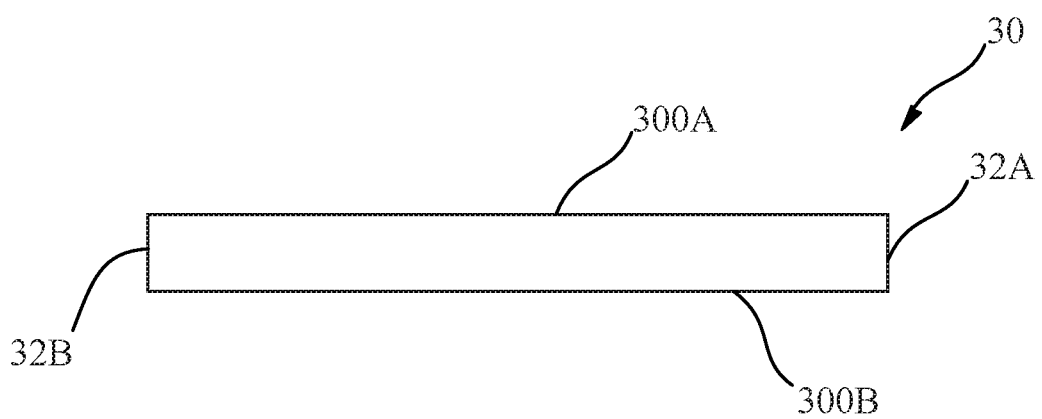
FIG. 3 is a schematic representation of an elevation view of a fluid management layer constructed in accordance with the present disclosure.
Figure 4:
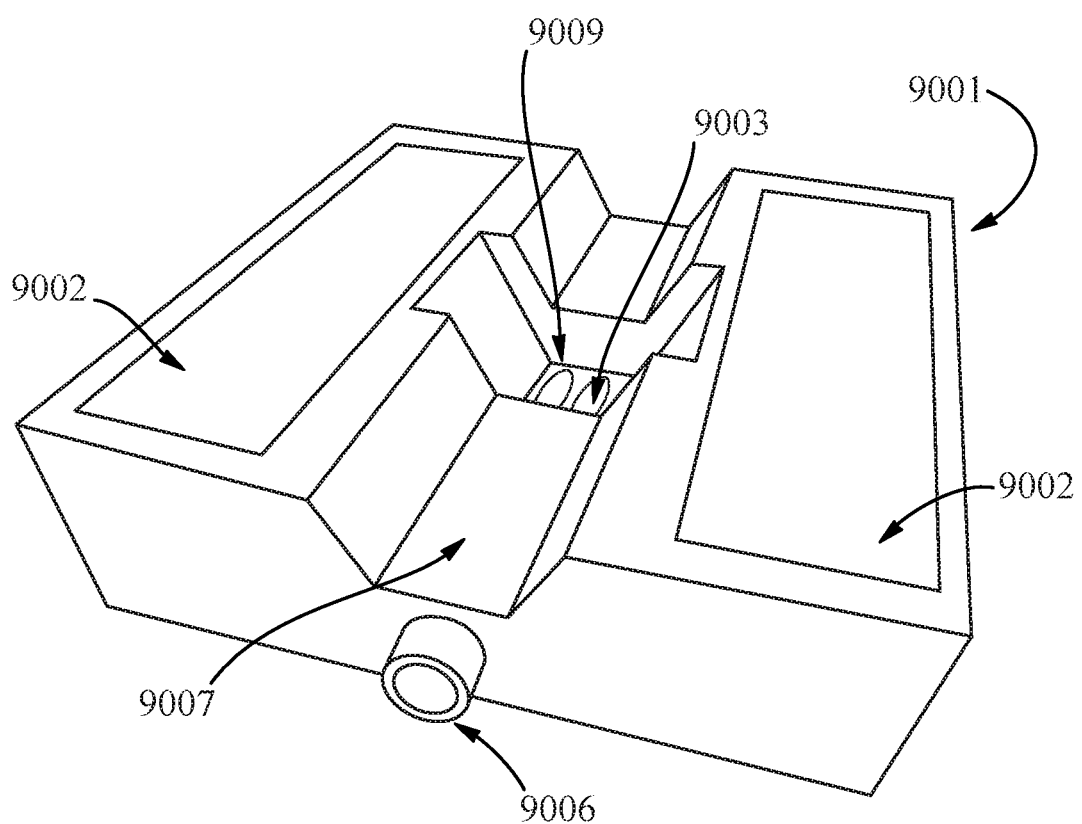
FIGS. 4-6B are schematic representations showing an apparatus for carrying out the Repetitive Acquisition Time and Rewet test method.
Figure 5A:
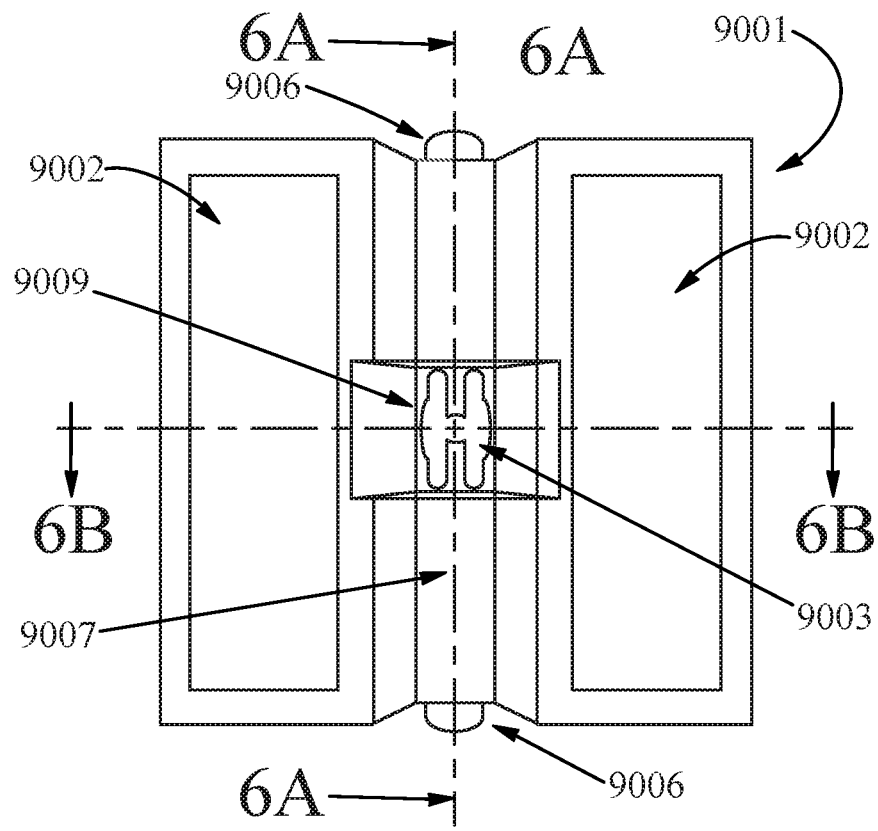
Figure 5B:
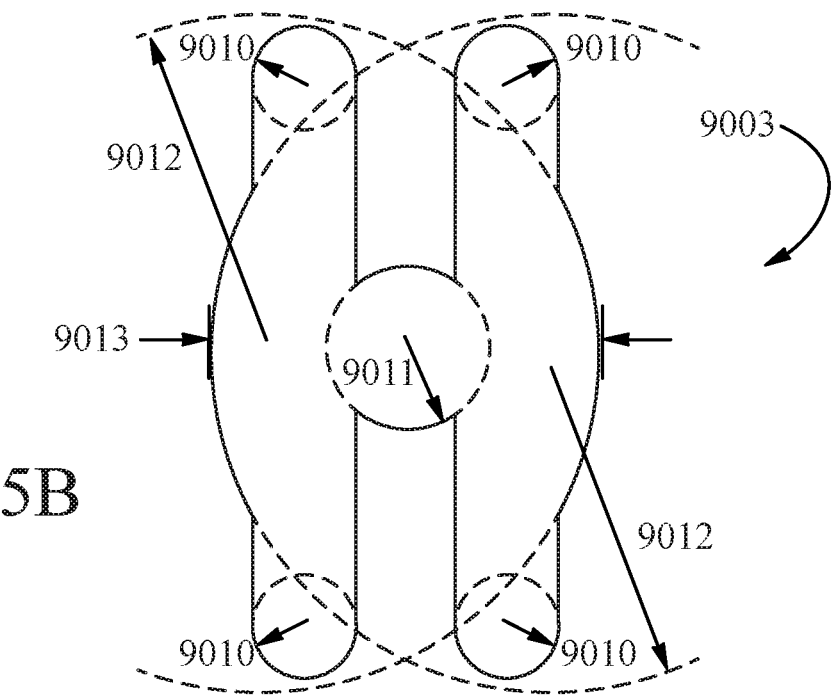
Figure 6A:
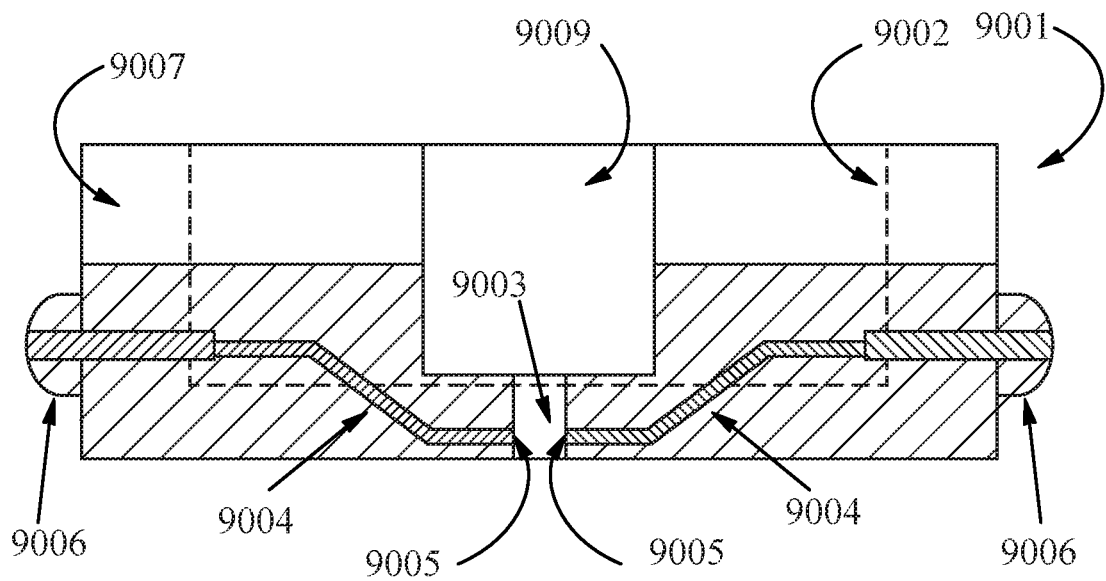
Figure 6B:
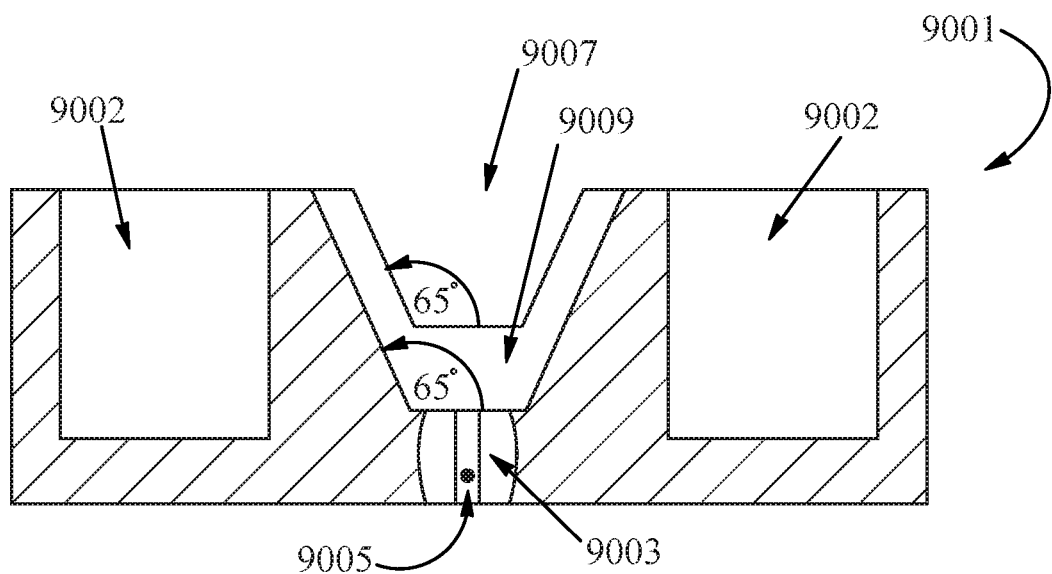

Referring now to FIG. 3, typically, caliper on spunlace lines can range from about 0.03 mm per 10 gsm to about 0.12 mm per 10 gsm. In conventional, spunlace lines, webs are hit from multiple water jets on the first surface 300A and the second surface 300B. Additionally, the web is typically wound around a variety of rolls such that additional water jets can further entangle the constituent fibers of the strata. Additionally, these webs may be wound around roll dryers. However, the inventors have found that winding of the web around these rolls causes compression on the web and actually reduces the caliper of the web. By reducing the number of rolls upon which the web is wound during processing, the inventors have been able to increase the caliper of integrated web which in turn equals a higher caliper on the fluid management layers of the present disclosure.

So unlike traditional spunlace materials, the fluid management layers of the present disclosure can have a caliper factor (mm of caliper per 10 gsm) of at least about 0.13 mm, at least about 0.15, or about 0.2 mm, including any values within these ranges and any ranges created thereby. The fluid management layer 30 can have a caliper factor of between 0.13 mm to about 0.3 mm, or from about 0.14 mm to about 0.25 mm, or from about 0.15 mm to about 0.22 mm, including all values within these ranges and any ranges created thereby. Caliper data is provided hereafter for a variety of samples.

It is worth noting that conventional spunlace lines are typically able to handle basis weights which go up to about 110 gsm of material. This limitation is in part due to the capacity of the carding machines. There have been experiments in the past, run by one or more of the inventors, with basis weights of over 130 gsm on conventional spunlace lines which achieved a caliper of 0.24 mm per 10 gsm; however, these experiments were done using multiple passes under the carding machines. Basically, the web from carding machines was integrated and the re-looped under the carding machines and integrated again. So, it is believed that the caliper effect was due, in large part, to the spacing between the first pass and the second pass.

Additionally, the caliper factors above were derived from caliper data from material which was rolled for storage/shipping. Caliper measures pre-winding could be taken which would yield much higher caliper factors. However, such caliper measurements may not necessarily reflect the fluid management layer that makes it into an article.

The inventors have also found that this processing technique can be utilized not only on spunlace materials where the strata are heterogeneous but also where the strata are homogeneous, e.g. each stratum has the same fiber makeup. Additionally, the inventors have surprisingly found that spunlace materials constructed with this process can also provide good resiliency and recovery from compression above those spunlace materials that are produced via conventional lines. Additionally, with the appropriate fiber selection, the inventors have also found that along with the increased caliper, good compressive recovery is also attainable. Fiber selection and compression recovery data for a variety of samples is also provided below.

In contrast to the 130 gsm experiments mentioned heretofore, the fluid management layers of the present disclosure can have a basis weight of up to 75 grams per square meter (gsm); or a basis weight of up to 70 gsm; or a basis weight in the range of about 40 gsm to about 75 gsm; or in the range of about 50 gsm to about 70 gsm; or in the range of about 55 gsm to about 65 gsm, including any values within these ranges and any ranges created thereby. In another specific example, the fluid management layer 30 may have a basis weight of between 40 gsm to 60 gsm.

Some absorbent articles may not require as much basis weight as recited above. For example, liners which generally do not have the same level of absorbent capacity as menstrual pads may be able to have a reduced basis weight over that which was recited above. For example, the fluid management layer may have a basis weight of between 30 gsm to 70 gsm, between 35 gsm to about 65 gsm, or from about 40 gsm to about 60 gsm, specifically including all values within these ranges and any ranges created thereby. In one specific example, the fluid management layer of the present disclosure can have a basis weight of about 55 gsm.

Still referring to FIGS. 1A-3, due to the fiber integration, the fluid management layer 30 does not require adhesives or latex binders for stability. Additionally, the carded staple-fiber nonwoven of the fluid management layers of the present disclosure can be manufactured from an assortment of suitable fiber types that produce the desired performance characteristics which is discussed in additional detail below.

As will be discussed in additional detail below, the types of fibers in the fluid management layer of the present disclosure are described in terms of their functionality within the fluid management layer. For example, absorbent fibers are utilized to absorb liquid insults. Stiffening fibers are utilized to bond together via heat treatment thereby providing stiffness to the fluid management layer. Resilient fibers are utilized to provide recovery from compressive forces which act against the fluid management layer.

In order to enhance the stabilizing effect of the integration, crimped fibers may be utilized. As discussed in additional detail below, the fluid management layers of the present disclosure may comprise absorbent fibers, stiffening fibers, and resilient fibers. One or more of these fibers may be crimped prior to integration. For example, where synthetic fibers are utilized, these fibers may be mechanically crimped via intermeshing teeth. And for the absorbent fibers, these fibers may be mechanically crimped and/or may have a chemically induced crimp due to the variable skin thickness formed during creation of the absorbent fibers.

Overall the fluid management layers of the present disclosure may comprise from about 15 percent to about 60 percent by weight, from about 20 percent to about 50 percent by weight, from about 25 percent to about 40 percent by weight, specifically including any values within these ranges and any ranges created thereby of absorbent fibers. In one specific example, fluid management layers may comprise about 30 percent by weight of absorbent fibers.

Similarly, overall the fluid management layers of the present disclosure may comprise from about 20 percent to about 70 percent, from about 30 percent to about 60 percent, from about 35 percent to about 50 percent by weight of resilient fibers, specifically reciting all values within these ranges and any ranges created thereby. In one specific example, fluid management layers may comprise about 40 percent by weight resilient fibers.

And, the fluid management layers of the present disclosure may comprise from about 15 percent to about 60 percent, from about 20 percent to about 50 percent, or from about 25 percent to about 40 percent of stiffening fiber, specifically reciting all values within these ranges and any ranges created thereby. In one specific example, the fluid management layer 30 may comprise about 30 percent by weight stiffening fibers.

For fluid management layers of the present disclosure, the weight percentage of stiffening fibers can be greater than or equal to the weight percentage of resilient fibers. The weight percentage of absorbent fibers can be less than the weight percentage of resilient fibers and/or stiffening fibers. In general, a higher weight percentage of absorbent fibers is considered to be beneficial in rapidly absorbent fluid insults; however, given the proximity of the absorbent fibers to the topsheet, it is beneficial for the absorbent core to dewater the absorbent fibers. Where there is a larger percentage of absorbent fibers, typically a larger core is required to dewater the absorbent fibers. This typically leads to higher costs. With this in mind, a ratio of absorbent fibers in the fluid management layers of the present disclosure to stiffening fibers by weight percentage is less than 1:1, less than 0.6:1, or less than 0.5:1, specifically reciting all values within these ranges and any ranges created thereby. Similarly, a ratio of absorbent fibers in the fluid management layers of the present disclosure to resilient fibers by weight percentage is less than 1:1, less than 0.8:1, or less than 0.7:1, specifically reciting all values within these ranges and any ranges created thereby.

Regardless of whether the fluid management layer is utilized in an adult incontinence article or a menstrual article, of critical importance is the ability of the fluid management layer to acquire liquid insults from the topsheet and to pull the liquid far enough from the topsheet, such that the topsheet does not feel wet. To accomplish this, the inventors have found that the caliper increase discussed herein can facilitate fluid acquisition due to the increased void volume of the fluid management layer. The higher caliper at the lower basis weight equals more void volume which can facilitate fluid acquisition. It is important however, to balance caliper and capillarity. So, while the increased caliper can provide a cushiony fluid management layer, without the appropriate fiber selection for capillarity (particularly in the menstrual context), the fluid management layer would not be very effective form a fluid handling standpoint.

Additionally, the increased caliper of the fluid management layer can also provide a stain masking benefit. Namely, the stains that are visible through the topsheet with absorbent articles using the fluid management layer of the present disclosure, appear much smaller and less red than their conventional fluid management layer counterparts. Stain size data is provided hereafter.

Referring back to the discussion regarding void volume, for a set basis weight of a fiber, larger diameter fibers can provide more void volume between adjacent fibers as compared to their smaller diameter counterparts. As such, the fiber size of the fibers in the strata closest to the topsheet may also be important. Namely, if the diameters of too many of the fibers in the first carded nonwoven and/or the second carded nonwoven are too small, this could detrimentally impact the permeability and the void volume that is created for rapid fluid acquisition (assuming the first carded nonwoven and the second carded nonwoven are more proximal to the topsheet than the third carded nonwoven).

Ideally, particularly in the context of menstrual fluid, the fluid management layer can have sufficient capillarity to drain the topsheet. Capillarity is driven by small pores; however, too small of pores decreases permeability which could also negatively impact acquisition speed and cause a wet feeling topsheet.

With the above in mind, the inventors have carefully selected not only the fibers types in each of the strata in the fluid management layers of the present disclosure but have also carefully selected the diameters of the fiber types. The fiber types of the individual strata are discussed in additional detail hereafter. It worth noting that the discussion below regarding fiber types in the strata of the fluid management layer assumes that the first carded nonwoven web is nearer to the topsheet than the second carded nonwoven web and/or third carded nonwoven web.

Any suitable linear density of absorbent fiber may be utilized. For example, the absorbent fiber linear densities may range from about 1 dtex to about 7 dtex, about 1.4 dtex to about 6 dtex, or from about 1.7 dtex to about 5 dtex, specifically reciting all values within these ranges and any ranges created thereby. In one specific example, the absorbent fiber may comprise a linear density of about 1.7 dtex.

The absorbent fibers of the fluid management layers of the present disclosure may have any suitable shape. Some examples include trilobal, "H," "Y," "X," "T," or round. Further, the absorbent fibers can be solid, hollow or multi-hollow. Other examples of suitable multi-lobed, absorbent fibers for utilization in the carded staple-fiber nonwovens detailed herein are disclosed in U.S. Pat. No. 6,333,108 to Wilkes et al, U.S. Pat. No. 5,634,914 to Wilkes et al., and U.S. Pat. No. 5,458,835 to Wilkes et al. The trilobal shape can improve wicking and improve masking. Suitable trilobal rayon is available from Kelheim Fibres and sold under the trade name Galaxy. While each stratum may comprise a different shape of absorbing fiber, much like mentioned above, not all carding equipment may be suited to handle such variation between/among strata. In one specific example, the fluid management layer comprises round absorbent fibers.

Any suitable absorbent fibers may be utilized. Some conventional absorbent fibers include cotton, rayon or regenerated cellulose or combinations thereof. In one example, the fluid management layer may comprise viscose cellulose fibers. The absorbent fibers may comprise staple-length fibers. The staple length of the absorbent fibers can be in the range of about 20 mm to about 100 mm, or about 30 mm to about 50 mm or about 35 mm to about 45 mm, specifically reciting all values within these ranges and any ranges created thereby.

As noted previously, in addition to absorbent fibers, fluid management layer may also comprise stiffening fibers. Stiffening fibers may be utilized to help provide structural integrity to the fluid management layer. The stiffening fibers can help increase structural integrity of the fluid management layer in a machine direction and in a cross-machine direction which can facilitate web manipulation during processing of the fluid management layer for incorporation into a disposable absorbent article. With that in mind, the constituent material of the stiffening fibers, the weight percentage of the stiffening fibers, and heat of processing should be carefully selected. The heat stiffening process is discussed hereafter.

Any suitable linear density of stiffening fiber may be utilized. For example, the stiffening fiber linear density may range from about 1.7 dtex to about 12 dtex, from about 4 dtex to about 10 dtex, or from about 5 dtex to about 7 dtex, specifically reciting all values within these ranges and any ranges created thereby. In one specific example, the stiffening fibers may comprise linear density of about 5.8 dtex.

Any suitable stiffening fiber may be utilized. Some examples of suitable stiffening fibers include bi-component fibers comprising polyethylene and polyethylene terephthalate components or polyethylene terephthalate and co-polyethylene terephthalate components. The components of the bi-component fiber may be arranged in a core sheath arrangement, a side by side arrangement, an eccentric core sheath arrangement, a trilobal arrangement, or the like. In one specific example, the stiffening fibers may comprise bi-component fibers having polyethylene/polyethylene terephthalate components arranged in a concentric, core-sheath arrangement where the polyethylene is the sheath.

While other materials may be useful in creating a resilient structure, the inventors have found that the stiffness of polyethylene terephthalate is needed to create a resilient structure. In contrast, the polyethylene component of the stiffening fibers can be utilized to bond to one another during heat treatment. This can help provide tensile strength to the web in both the MD and CD. Additionally, the bonding of the polyethylene component to other polyethylene components of stiffening fibers can create fixed points in the nonwoven. These fixed points can reduce the amount of fiber-to-fiber sliding which can increase the resiliency of the material.

One of the benefits of the stiffening fibers is that the integrated nonwoven may be heat treated post fiber entanglement. The heat treatment can provide additional structural integrity to the integrated nonwoven by forming bonds between adjacent stiffening fibers. So, where there is a higher percentage of stiffening fibers, more connection points may be created. However, too many connection points can yield a much stiffer fluid management layer which may negatively impact comfort. As such, the weight percentage of the stiffening fibers can be important when designing an absorbent article.

Regarding the heat stiffening process, any suitable temperature may be utilized. And, the suitable temperature may be impacted, in part, by the constituent chemistry of the stiffening fibers as well as by the processing fluid management layer web. The fluid management layer web may be heat stiffened at a temperature of 132 degrees Celsius. It is also worth noting, that in order to provide a uniform stiffness property across the fluid management layer, any heating operation should be set up to provide uniform heating to the fluid management layer web. Even small variations in temperature can greatly impact the tensile strength of the fluid management layer.

As noted previously, the fluid management layer of the present disclosure may additionally comprise resilient fibers. The resilient fibers can help the fluid management layer maintain its permeability and compression recovery. Any suitable size fiber may be utilized. For example, the resilient fibers can have a linear density of about 1 dtex to about 12 dtex, from about 2 dtex to about 7 dtex, or from about 3 dtex to about 5 dtex, specifically reciting all values within these ranges and any ranges created thereby. In one specific example, the resilient fibers may comprise a linear density of about 4.4 dtex. In another specific example, the fluid management layer may comprise resilient fibers having variable cross sections, e.g. round and hollow spiral, and/or may comprise resilient fibers having variable dtex's.

The resilient fibers can be any suitable thermoplastic fiber, such as polypropylene (PP), polyethylene terephthalate, or other suitable thermoplastic fibers known in the art. The staple length of the resilient fibers can be in the range of about 20 mm to about 100 mm, or about 30 mm to about 50 mm or about 35 mm to about 45 mm. The thermoplastic fibers can have any suitable structure or shape. For example, the thermoplastic fibers can be round or have other shapes, such as spiral, scalloped oval, trilobal, scalloped ribbon, and so forth. Further, the PP fibers can be solid, hollow or multi-hollow. The resilient fibers may be solid and round in shape. Other suitable examples of resilient fibers include polyester/co-extruded polyester fibers. Additionally, other suitable examples of resilient fibers include bi-component fibers such as polyethylene/polypropylene, polyethylene/polyethylene terephthalate, polypropylene/polyethylene terephthalate. These bi-component fibers may be configured as a sheath and a core. The bi-component fibers may provide a cost-effective way to increase basis weight of the material while additionally enabling optimization of the pore size distribution.

The resilient fibers can be polyethylene terephthalate (PET) fibers, or other suitable non-cellulosic fibers known in the art. The PET fibers can have any suitable structure or shape. For example, the PET fibers can be round or have other shapes, such as spiral, scalloped oval, trilobal, scalloped ribbon, hollow spiral, and so forth. Further, the PET fibers can be solid, hollow or multi-hollow. In one particular example, fibers may be fibers made of hollow/spiral PET. Optionally, the resilient fibers may be spiral-crimped or flat-crimped. The resilient fibers may have a crimp value of between about 4 and about 12 crimps per inch (cpi), or between about 4 and about 8 cpi, or between about 5 and about 7 cpi, or between about 9 and about 10 cpi. Particular non-limiting examples of resilient fibers can be obtained from Wellman, Inc. Ireland under the trade names H1311 and T5974. Other examples of suitable resilient fibers for utilization in the carded staple-fiber nonwovens detailed herein are disclosed in U.S. Pat. No. 7,767,598 to Schneider et al.

It is worth noting that the stiffening fibers and resilient fibers should be carefully selected. For example, while the constituent chemistries of the stiffening fibers and the resilient fibers may be similar, resilient fibers should be selected such that their constituent material's melting temperature is higher than that of the stiffening fibers. Otherwise, during heat treatment, resilient fibers would bond to stiffening fibers and vice versa and could create an overly rigid structure. Note that where the stiffening fibers comprise bicomponent fibers, i.e. core/sheath configuration, the resilient fibers may comprise the constituent chemistry of the core.

Samples were created and analyzed regarding a variety of characteristics. Note that the gsm mentioned in the description of the sample is a target gsm, while the measured gsm is in Table 1. It is also worth noting that each of Samples 1-4 was created utilizing the process described herein which provides increased caliper per gsm of material over conventional processing. Each of Samples 1-4 comprised two carded webs that were integrated, and the two carded webs comprised the same fiber blend, i.e. homogeneous configuration.

Sample 1: a 55 gsm spunlace material which comprised 30 percent by weight viscose cellulose, 1.7 dtex; 40 percent by weight polyethylene terephthalate, 4.4 dtex; and 30 percent by weight polyethylene terephthalate/polyethylene bico, 2.2 dtex.

Sample 2: a 55 gsm spunlace material which comprised 30 percent by weight viscose cellulose, 1.7 dtex; 40 percent by weight polyethylene terephthalate, 4.4 dtex; and 30 percent by weight polyethylene terephthalate/polyethylene bico, 5.8 dtex.

Sample 3: a 55 gsm spunlace material which comprised 30 percent by weight viscose cellulose, 1.7 dtex; 40 percent by weight polyethylene terephthalate, 10 dtex; and 30 percent by weight polyethylene terephthalate/polyethylene bico, 2.2 dtex.

Sample 4: a 55 gsm spunlace material which comprised 30 percent by weight viscose cellulose, 1.7 dtex; 35 percent by weight polyethylene terephthalate, 6.7 dtex; and 35 percent by weight polyethylene terephthalate/polyethylene bico, 5.8 dtex.

Sample 5: a 50 gsm conventional spunlace material which comprised 40 percent by weight viscose cellulose, 1.7 dtex; 20 percent by weight polyethylene terephthalate fibers, 4.4 dtex; and 40 percent by weight polypropylene/polyethylene bico fibers, 1.7 dtex.

Sample 6: a 75 gsm conventional spunlace processing: first and second strata are homogeneous, with each having 20 percent viscose rayon round, 1.7 dtex; 40 percent polyethylene terephthalate/polyethylene bico, 5.8 dtex; and 40 percent hollow spiral, polyethylene terephthalate fibers, 10 dtex. The third stratum had 80 percent viscose rayon, 1.7 dtex and 20 percent polyethylene terephthalate hollow spiral fibers, 10 dtex.

Sample 7: a 70 gsm conventional spunlace processing: first and second strata are homogenous with each having 20 percent by weight viscose cellulose, 1.7 dtex; 30 percent by weight polyethylene terephthalate/copolyethylene terephthalate bico, 7 dtex; and 50 percent polyethylene terephthalate hollow spiral fibers, 10 dtex.

Each of the samples was evaluated for a number of properties. Table 1 show the results of the Compression Caliper method disclosed herein on the Samples 1-7.

TABLE 1

| Sample No. | Basis Weight (gsm) | Caliper (mm) | Total Compression (mm) | Total Recovery (mm) | Percent Recovery | Caliper factor (mm/10 gsm) | Density (g/cc) |
|---|---|---|---|---|---|---|---|
| Sample No. 1 | 58.11 | 0.73 | 0.43 | 0.37 | 85 | 0.13 | 0.080 |
| Sample No. 2 | 51.86 | 0.93 | 0.54 | 0.45 | 84 | 0.18 | 0.056 |
| Sample No. 3 | 55.96 | 1.14 | 0.49 | 0.41 | 83 | 0.20 | 0.049 |
| Sample No. 4 | 52.27 | 1.14 | 0.55 | 0.48 | 87 | 0.22 | 0.046 |
| Sample No. 5 | 51.52 | 0.54 | 0.16 | 0.15 | 90 | 0.10 | 0.095 |
| Sample No. 6 | 77.29 | 0.71 | 0.27 | 0.24 | 89 | 0.09 | 0.109 |
| Sample No. 7 | 74.06 | 0.89 | 0.27 | 0.25 | 98 | 0.12 | 0.083 |

Recall that Samples 1-4 represent nonwoven material constructed in accordance with the present disclosure while Samples 5-7 are nonwoven materials which are either commercially available or made via conventional spunlace processing. As shown in Table 1, the Total Compression of Samples 1-4 was, in most cases at least double the Total Compression of Samples 5-7. The fluid management layers of the present disclosure may exhibit a total compression of greater than 0.35 mm, greater than 0.40 mm, or greater than 0.42 mm, specifically including all values within these ranges and any ranges created thereby. The fluid management layers of the present disclosure may also exhibit a total recovery of at least 0.30, at least 0.33 mm, or at least 0.35 mm, specifically including all values within these ranges and any ranges created thereby. For the sake of convenience, the Total Compression, Total Recovery, and Percent Recovery were derived from the data in Table 2.

Fluid management layers of the present disclosure may exhibit a total compression of between about 0.40 mm and about 0.70 mm, between about 0.41 and about 0.70 mm, between about 0.43 and 0.7 mm, specifically including all values within these ranges and any ranges created thereby. The fluid management layers of the present disclosure may exhibit a total recovery of at between about 0.35 and about 0.7 mm, between about 0.36 mm and about 0.70 mm, and between about 0.37 and about 0.70 mm, specifically including all values within these ranges and any ranges created thereby. The fluid management layers of the present disclosure may exhibit a caliper decrease of at least about 0.13 mm, at least about 0.15 mm, at least about 0.17 mm as a final caliper as measured at 1 kPa from 0.5 kPa, specifically including all values within these ranges and any ranges created thereby. The fluid management layers of the present disclosure may exhibit a caliper decrease of between about 0.13 mm to about 0.30 mm, from about 0.15 mm to about 0.30 mm, from about 0.17 mm to about 0.30 mm, as a final caliper as measured at 1 kPa from 0.5 kPa, specifically including all values within these ranges and any ranges created thereby. The fluid management layers of the present disclosure may exhibit a caliper decrease of at least about 0.20 mm, at least about 0.25 mm, at least about 0.30 mm, as a final caliper as measured at 2 kPa from 0.5 kPa, specifically including all values within these ranges and any ranges created thereby. The fluid management layers of the present disclosure may exhibit a caliper decrease of between about 0.20 mm and about 0.50 mm, between about 0.21 mm and about 0.50 mm, and about 0.25 mm to about 0.50 mm, as a final caliper as measured at 2 kPa from 0.5 kPa, specifically including all values within these ranges and any ranges created thereby. The fluid management layers of the present disclosure may exhibit a caliper decrease of at least about 0.25 mm, at least about 0.30 mm, at least about 0.35 mm, as a final caliper measured at 3 kPa from 0.5 kPa, specifically including all values within these ranges and any ranges created thereby. The fluid management layers of the present disclosure may exhibit a caliper decrease of between about 0.25 mm to about 0.60 mm, from between about 0.30 mm to about 0.60 mm, or from between about 0.35 mm to about 0.60 mm, as a final caliper as measured from 3 kPa from 0.5 kPa, specifically including all values within these ranges and any ranges created thereby.

As shown, fluid management layers of the present disclosure can have a density of less or equal to 0.080 g/cc. For example, fluid management layers of the present disclosure can have a density of from between 0.020 g/cc to 0.080, from 0.030 g/cc to 0.070 g/cc, or from 0.035 g/cc to 0.065 g/cc, specifically including all values within these ranges and any ranges created thereby.

Additional data regarding the compression test for each of the samples is provided below in Table 2. The caliper of each of the Samples is provided below in mm at the various pressures as measured via the Compression Caliper method described herein.

TABLE 2

| Sample No. | 0.5 kPa | 1 kPa | 2 kPa | 3 kPa | 5 kPa | 0.5 kPa |
|---|---|---|---|---|---|---|
| Sample 1 | 0.83 | 0.67 | 0.56 | 0.48 | 0.39 | 0.76 |
| Sample 2 | 0.93 | 0.74 | 0.58 | 0.49 | 0.39 | 0.84 |
| Sample 3 | 1.14 | 0.97 | 0.82 | 0.74 | 0.65 | 1.06 |
| Sample 4 | 1.14 | 0.94 | 0.78 | 0.68 | 0.59 | 1.07 |
| Sample 5 | 0.54 | 0.48 | 0.44 | 0.41 | 0.38 | 0.52 |
| Sample 6 | 0.71 | 0.63 | 0.55 | 0.50 | 0.44 | 0.68 |
| Sample 7 | 0.89 | 0.81 | 0.73 | 0.68 | 0.62 | 0.87 |

As noted previously, where the fluid management layers are being designed for use within feminine hygiene articles, i.e. meant to handle menses, capillarity may be a useful. In general, higher capillarity equates to a lower air permeability value. Air permeability for the above samples is provided below in Table 3.

TABLE 3

| Sample No. | Air Permeability (m^3/m^2/min) | Standard Dev. |
|---|---|---|
| Sample 1 | 260.89 | 27.54 |
| Sample 2 | 340.00 | 25.87 |
| Sample 3 | 284.78 | 4.49 |
| Sample 4 | 355.38 | 12.17 |
| Sample 5 | 185.55 | |
| Sample 6 | 219.56 | 7.60 |
| Sample 7 | 318.22 | 10.78 |

However, the desire for increased caliper (to provide cushiony softness and masking) is diametrically opposed to the desire for high capillarity. So, there should be a balance between the caliper and capillarity. This balance is highlighted in Table 3.

Based on the data of Table 3, the air permeability of the fluid management layer can be between about 200 m^3/m^2/min and about 400 m^3/m^2/min, between about 220 m^3/m^2/min and about 375 m^3/m^2/min, or between about 240 m^3/m^2/min and about 370 m^3/m^2/min, specifically including all values within these ranges and any ranges created thereby.

Recall that an additional benefit of the fluid management layers of the present disclosure was stain masking. Data provided in Table 4 shows a reduced stain size for the fluid management layers of the present disclosure. For the stain size data below, each of the Samples listed were utilized in an absorbent article having a topsheet that was a hydroformed film with microapertures and macroapertures. The film is currently available from Tredegar Corp. USA. And each of these absorbent articles had an absorbent core which was an airlaid absorbent core comprising pulp fibers, absorbent gelling material, and bico fibers, having a basis weight of 163 gsm available from Glatfelter, York, PA, USA.

TABLE 4

| Sample No. | Stain Size (cm^2) |
|---|---|
| 1 | 36.97 |
| 2 | 45.02 |
| 3 | 36.13 |
| 4 | 40.64 |
| 5 | 54.01 |

As shown, the stain size for the fluid management layers of the present disclosure are smaller than that of the conventional material. The stain size in of absorbent articles in accordance with the present description may be less than 50 cm^2, less than 47 cm^2, or less than 40 cm^2, specifically reciting all values within these ranges and any ranges created thereby. The stain size exhibited the absorbent articles of the present disclosure can be between about 30 cm^2 to about 50 cm^2, from about 30 cm^2 to about 46 cm^2, or from about 30 cm^2 to about 42 cm^2, specifically reciting all values within these ranges and any ranges created thereby. For each of the articles tested, the fluid management layer was disposed between the topsheet and the absorbent core.

While the fluid management layers of the present disclosure can provide the user with a soft, more cushiony feeling absorbent article, the fluid management layers of the present disclosure also provide the user with the appropriate stiffness such that their resultant absorbent articles can reduce the likelihood of bunching. A metric which can determine the stiffness of a fluid management layer is MD Bending Length. Data is provided below in Table 5 regarding Samples 1-4.

TABLE 5

| Sample No. | MD Bending Length (mN/cm) |
|---|---|
| Sample 1 | 2.27 |
| Sample 2 | 1.23 |
| Sample 3 | 2.52 |
| Sample 4 | 1.62 |
| Sample 5 | 7.3 |

The fluid management layers of the present disclosure may have an MD Bending Length of from between about 1 mN/cm to about 12 mN/cm, from about 1.2 mN/cm to about 12 mN/cm, or from about 1.3 mN/cm to about 12 mN/cm, specifically reciting all values within these ranges and any ranges created thereby.

Absorbent Articles

Referring back to FIGS. 1A and 1B, as mentioned previously, disposable absorbent articles of the present disclosure may comprise the topsheet 20 and the backsheet 50. Sandwiched therebetween may be the fluid management layer 30 and the absorbent core 40. Additional layers may be positioned between the topsheet 20 and the backsheet 50.

The topsheet 20 may be joined to the backsheet 50 by attachment methods (not shown) such as those well known in the art. The topsheet 20 and the backsheet 50 may be joined directly to each other in the article periphery and may be indirectly joined together by directly joining them to the absorbent core 40, the fluid management layer 30, and/or additional layers disposed between the topsheet 20 and the backsheet 50. This indirect or direct joining may be accomplished by attachment methods which are well known in the art.

The topsheet 20 may be compliant, soft feeling, and non-irritating to the wearer's skin. Suitable topsheet materials include a liquid pervious material that is oriented towards and contacts the body of the wearer permitting bodily discharges to rapidly penetrate through it without allowing fluid to flow back through the topsheet to the skin of the wearer. The topsheet, while being capable of allowing rapid transfer of fluid through it, may also provide for the transfer or migration of the lotion composition onto an external or internal portion of a wearer's skin.

A suitable topsheet 20 can be made of various materials such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof.

Apertured film materials suitable for use as the topsheet include those apertured plastic films that are non-absorbent and pervious to body exudates and provide for minimal or no flow back of fluids through the topsheet. Nonlimiting examples of other suitable formed films, including apertured and non-apertured formed films, are more fully described in U.S. Pat. No. 3,929,135, issued to Thompson on Dec. 30, 1975; U.S. Pat. No. 4,324,246, issued to Mullane et al. on Apr. 13, 1982; U.S. Pat. No. 4,342,314, issued to Radel et al. on Aug. 3, 1982; U.S. Pat. No. 4,463,045, issued to Ahr et al. on Jul. 31, 1984; U.S. Pat. No. 5,006,394, issued to Baird on Apr. 9, 1991; U.S. Pat. No. 4,609,518, issued to Curro et al. on Sep. 2, 1986; and U.S. Pat. No. 4,629,643, issued to Curro et al. on Dec. 16, 1986.

Nonlimiting examples of woven and nonwoven materials suitable for use as the topsheet include fibrous materials made from natural fibers, e.g. cotton, including 100 percent organic cotton, modified natural fibers, synthetic fibers, or combinations thereof. These fibrous materials can be either hydrophilic or hydrophobic, but it is preferable that the topsheet be hydrophobic or rendered hydrophobic. As an option, portions of the topsheet can be rendered hydrophilic, by the use of any known method for making topsheets containing hydrophilic components. Nonwoven fibrous topsheets 20 may be produced by any known procedure for making nonwoven webs, nonlimiting examples of which include spunbonding, carding, wet-laid, air-laid, meltblown, needle-punching, mechanical entangling, thermo-mechanical entangling, and hydroentangling.

The topsheet 20 may be formed from a combination of an apertured film and a nonwoven. For example, a film web and a nonwoven web can be combined as described in U.S. Pat. No. 9,700,463. Alternatively, a film may be extruded onto a nonwoven material which is believed to provide enhanced contact between the film layer and the nonwoven material. Exemplary processes for such a combination are described in U.S. Pat. Nos. 9,849,602 and 9,700,463.

The backsheet 50 may be positioned adjacent a garment-facing surface of the absorbent core 40 and may be joined thereto by attachment methods such as those well known in the art. For example, the backsheet 50 may be secured to the absorbent core 40 by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are known in the art.

The backsheet 50 may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet 207 may prevent, or at least inhibit, the exudates absorbed and contained in the absorbent core 205 from wetting articles of clothing which contact the incontinence pad 10 such as undergarments. However, the backsheet 50 may permit vapors to escape from the absorbent core 40 (i.e., is breathable) while in some cases the backsheet 50 may not permit vapors to escape (i.e., non-breathable). Thus, the backsheet 50 may comprise a polymeric film such as thermoplastic films of polyethylene or polypropylene. A suitable material for the backsheet 50 is a thermoplastic film having a thickness of from about 0.012 mm (0.5 mil) to about 0.051 mm (2.0 mils), for example. Any suitable backsheet known in the art may be utilized with the present invention.

The backsheet 50 acts as a barrier to any absorbed bodily fluids that may pass through the absorbent core 40 to the garment surface thereof with a resulting reduction in risk of staining undergarments or other clothing. A preferred material is a soft, smooth, compliant, liquid and vapor pervious material that provides for softness and conformability for comfort, and is low noise producing so that movement does not cause unwanted sound.

Exemplary backsheets are described in U.S. Pat. No. 5,885,265 (Osborn, III.) issued Mar. 23, 1999; U.S. Pat. No. 6,462,251 (Cimini) issued Oct. 8, 2002; U.S. Pat. No. 6,623,464 (Bewick-Sonntag) issued Sep. 23, 2003 or U.S. Pat. No. 6,664,439 (Arndt) issued Dec. 16, 2003. Suitable dual or multi-layer breathable backsheets for use herein include those exemplified in U.S. Pat. Nos. 3,881,489, 4,341,216, 4,713,068, 4,818,600, EP 203 821, EP 710 471, EP 710 472, and EP 793 952.

Suitable breathable backsheets for use herein include all breathable backsheets known in the art. In principle there are two types of breathable backsheets, single layer breathable backsheets which are breathable and impervious to liquids and backsheets having at least two layers, which in combination provide both breathability and liquid imperviousness. Suitable single layer breathable backsheets for use herein include those described for example in GB A 2184 389, GB A 2184 390, GB A 2184 391, U.S. Pat. Nos. 4,591,523, 3,989,867, 3,156,242 and WO 97/24097.

The backsheet may be a nonwoven web having a basis weight between about 20 gsm and about 50 gsm. In one embodiment, the backsheet is a relatively hydrophobic 23 gsm spunbonded nonwoven web of 4 denier polypropylene fibers available from Fiberweb Neuberger, under the designation F102301001. The backsheet may be coated with a non-soluble, liquid swellable material as described in U.S. Pat. No. 6,436,508 (Ciammaichella) issued Aug. 20, 2002.

The backsheet has a garment-facing side and an opposite body-facing side. The garment-facing side of the backsheet comprises a non-adhesive area and an adhesive area. The adhesive area may be provided by any conventional means. Pressure sensitive adhesives have been commonly found to work well for this purpose.

The absorbent core 40 of the present disclosure may comprise any suitable shape including but not limited to an oval, a discorectangle, a rectangle, an asymmetric shape, and an hourglass. For example, in some forms of the present invention, the absorbent core 205 may comprise a contoured shape, e.g. narrower in the intermediate region than in the end regions. As yet another example, the absorbent core may comprise a tapered shape having a wider portion in one end region of the pad which tapers to a narrower end region in the other end region of the pad. The absorbent core 40 may comprise varying stiffness in the MD and CD.

The configuration and construction of the absorbent core 40 may vary (e.g., the absorbent core 40 may have varying caliper zones, a hydrophilic gradient, a superabsorbent gradient, or lower average density and lower average basis weight acquisition zones). Further, the size and absorbent capacity of the absorbent core 40 may also be varied to accommodate a variety of wearers. However, the total absorbent capacity of the absorbent core 40 should be compatible with the design loading and the intended use of the disposable absorbent article or incontinence pad 10.

In some forms of the present invention, the absorbent core 40 may comprise a plurality of multi-functional layers that are in addition to the first and second laminates. For example, the absorbent core 40 may comprise a core wrap (not shown) useful for enveloping the first and second laminates and other optional layers. The core wrap may be formed by two nonwoven materials, substrates, laminates, films, or other materials. In a form, the core wrap may only comprise a single material, substrate, laminate, or other material wrapped at least partially around itself.

The absorbent core 40 of the present disclosure may comprise one or more adhesives, for example, to help immobilize the SAP or other absorbent materials within the first and second laminates.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen. These may be used to configure the superabsorbent layers.

Additions to the core of the present disclosure are envisioned. In particular, potential additions to the current multi-laminate absorbent core are described in U.S. Pat. No. 4,610,678, entitled "High-Density Absorbent Structures" issued to Weisman et al., on Sep. 9, 1986; U.S. Pat. No. 4,673,402, entitled "Absorbent Articles With Dual-Layered Cores", issued to Weisman et al., on Jun. 16, 1987; U.S. Pat. No. 4,888,231, entitled "Absorbent Core Having A Dusting Layer", issued to Angstadt on Dec. 19, 1989; and U.S. Pat. No. 4,834,735, entitled "High Density Absorbent Members Having Lower Density and Lower Basis Weight Acquisition Zones", issued to Alemany et al., on May 30, 1989. The absorbent core may further comprise additional layers that mimic the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345. These are useful to the extent they do not negate or conflict with the effects of the below described laminates of the absorbent core of the present invention.

Some examples of a suitable absorbent cores 40 that can be used in the absorbent article of the present disclosure is described in U.S. Patent Application Publication Nos. 2018/0098893 and 2018/0098891.

As noted previously, the absorbent articles comprising the fluid management layers of the present disclosure comprised a storage layer. Referring back to FIGS. 1A and 1B, the storage layer would generally be positioned where the absorbent core 40 is described. The storage layer may be constructed as described regarding absorbent cores. The storage layer can contain conventional absorbent materials. In addition to conventional absorbent materials such as creped cellulose wadding, fluffed cellulose fibers, Rayon fibers, wood pulp fibers also known as airfelt, and textile fibers, the storage layer often includes superabsorbent material that imbibes fluids and form hydrogels. Such materials are also known as absorbent gelling materials (AGM) and may be included in particle form. AGM is typically capable of absorbing large quantities of body fluids and retaining them under moderate pressures. Synthetic fibers including cellulose acetate, polyvinyl fluoride, polyvinylidene chloride, acrylics (such as ORLON), polyvinyl acetate, non-soluble polyvinyl alcohol, polyethylene, polypropylene, polyamides (such as nylon), polyesters, bicomponent fibers, tricomponent fibers, mixtures thereof and the like can also be used in the secondary storage layer. The storage layer can also include filler materials, such as PERLITE, diatomaceous earth, VERMICULITE, or other suitable materials, that lower rewet problems.

The storage layer or fluid storage layer may have absorbent gelling material (agm) in a uniform distribution or may have agm in a non-uniform distribution. The agm may be in the in the form of channels, pockets, stripes, criss-cross patterns, swirls, dots, or any other pattern, either two or three dimensional, that can be imagined by man. The AGM may be sandwiched between a pair of fibrous cover layers. Or AGM may be encapsulated, at least in part, by a single fibrous cover layer.

Portions of the storage layer can be formed only of superabsorbent material or can be formed of superabsorbent materials dispersed in a suitable carrier such as cellulose fibers in the form of fluff or stiffened fibers. One example of a non-limiting storage layer is a first layer formed only of superabsorbent material that is disposed on a second layer that is formed from a dispersion of superabsorbent material within cellulose fibers.

Detailed examples of absorbent cores formed of layers of superabsorbent material and/or layers of superabsorbent material dispersed within cellulose fibers that may be utilized in the absorbent articles (e.g., sanitary napkins, incontinence products) detailed herein are disclosed in U.S. Patent Publication No. 2010/0228209 A1. Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., WO 2012/052172 to Van Malderen, U.S. Pat. No. 8,466,336 to Carlucci, and U.S. Pat. No. 9,693,910 to Carlucci. These may be used to configure the secondary storage layer.

The absorbent article 10 may further comprise barrier cuffs. Some examples of other suitable barrier cuffs are described in U.S. Pat. Nos. 4,695,278; 4,704,115; 4,795,454; 4,909,803; U.S. Patent Application Publication No. 2009/0312730. Additional suitable barrier cuffs are described in U.S. Patent Application Publication Nos. 2018/0098893 and 2018/0098891.

Test Methods

Fiber Decitex (Dtex)

Textile webs (e.g. woven, nonwoven, airlaid) are comprised of individual fibers of material. Fibers are measured in terms of linear mass density reported in units of decitex. The decitex value is the mass in grams of a fiber present in 10,000 meters of that fiber. The decitex value of the fibers within a web of material is often reported by manufacturers as part of a specification. If the decitex value of the fiber is not known, it can be calculated by measuring the cross-sectional area of the fiber via a suitable microscopy technique such as scanning electron microscopy (SEM), determining the composition of the fiber with suitable techniques such as FT-IR (Fourier Transform Infrared) spectroscopy and/or DSC (Dynamic Scanning calorimetry), and then using a literature value for density of the composition to calculate the mass in grams of the fiber present in 10,000 meters of the fiber. All testing is performed in a room maintained at a temperature of 23° C.±2.0° C. and a relative humidity of 50%±2% and samples are conditioned under the same environmental conditions for at least 2 hours prior to testing.

If necessary, a representative sample of web material of interest can be excised from an absorbent article. In this case, the web material is removed so as not to stretch, distort, or contaminate the sample.

SEM images are obtained and analyzed as follows to determine the cross-sectional area of a fiber. To analyze the cross section of a sample of web material, a test specimen is prepared as follows. Cut a specimen from the web that is about 1.5 cm (height) by 2.5 cm (length) and free from folds or wrinkles. Submerge the specimen in liquid nitrogen and fracture an edge along the specimen's length with a razor blade (VWR Single Edge Industrial Razor blade No. 9, surgical carbon steel). Sputter coat the specimen with gold and then adhere it to an SEM mount using double-sided conductive tape (Cu, 3M available from electron microscopy sciences). The specimen is oriented such that the cross section is as perpendicular as possible to the detector to minimize any oblique distortion in the measured cross sections. An SEM image is obtained at a resolution sufficient to clearly elucidate the cross sections of the fibers present in the specimen. Fiber cross sections may vary in shape, and some fibers may consist of a plurality of individual filaments. Regardless, the area of each of the fiber cross sections is determined (for example, using diameters for round fibers, major and minor axes for elliptical fibers, and image analysis for more complicated shapes). If fiber cross sections indicate inhomogeneous cross-sectional composition, the area of each recognizable component is recorded and dtex contributions are calculated for each component and subsequently summed. For example, if the fiber is bi-component, the cross-sectional area is measured separately for the core and sheath, and dtex contribution from core and sheath are each calculated and summed. If the fiber is hollow, the cross-sectional area excludes the inner portion of the fiber comprised of air, which does not appreciably contribute to fiber dtex. Altogether, at least 100 such measurements of cross-sectional area are made for each fiber type present in the specimen, and the arithmetic mean of the cross-sectional area $a_k$ for each are recorded in units of micrometers squared ($\mu m^2$) to the nearest 0.1 $\mu m^2$.

Fiber composition is determined using common characterization techniques such as FTIR spectroscopy. For more complicated fiber compositions (such as polypropylene core/polyethylene sheath bi-component fibers), a combination of common techniques (e.g. FTIR spectroscopy and DSC) may be required to fully characterize the fiber composition. Repeat this process for each fiber type present in the web material.

The decitex $d_k$ value for each fiber type in the web material is calculated as follows:

$$d_k = 10000 \text{ m} \times a_k \times \rho_k \times 10^{-6}$$

where $d_k$ is in units of grams (per calculated 10,000 meter length), $a_k$ is in units of $\mu m^2$, and $\rho_k$ is in units of grams per cubic centimeter (g/cm$^3$). Decitex is reported to the nearest 0.1 g (per calculated 10,000 meter length) along with the fiber type (e.g. PP, PET, cellulose, PP/PET bico).

Basis Weight

The basis weight of a test sample is the mass (in grams) per unit area (in square meters) of a single layer of material and is measured in accordance with compendial method WSP 130.1. The mass of the test sample is cut to a known area, and the mass of the sample is determined using an analytical balance accurate to 0.0001 grams. All measurements are performed in a laboratory maintained at 23° C.±2 C.° and 50%±2% relative humidity and test samples are conditioned in this environment for at least 2 hours prior to testing.

Measurements are made on test samples taken from rolls or sheets of the raw material, or test samples obtained from a material layer removed from an absorbent article. When excising the material layer from an absorbent article, use care to not impart any contamination or distortion to the layer during the process. The excised layer should be free from residual adhesive. To ensure that all adhesive is removed, soak the layer in a suitable solvent that will dissolve the adhesive without adversely affecting the material itself. One such solvent is THF (tetrahydrofuran, CAS 109-99-9, for general use, available from any convenient source). After the solvent soak, the material layer is allowed to thoroughly air dry in such a way that prevents undue stretching or other deformation of the material. After the material has dried, a test specimen is obtained. The test specimen must be as large as possible so that any inherent material variability is accounted for.

Measure the dimensions of the single layer test specimen using a calibrated steel metal ruler traceable to NIST, or equivalent. Calculate the Area of the test specimen and record to the nearest 0.0001 square meter. Use an analytical balance to obtain the Mass of the test specimen and record to the nearest 0.0001 gram. Calculate Basis Weight by dividing Mass (in grams) by Area (in square meters) and record to the nearest 0.01 grams per square meter (gsm). In like fashion, repeat for a total of ten replicate test specimens. Calculate the arithmetic mean for Basis Weight and report to the nearest 0.01 grams/square meter.

Air Permeability

The measurements for air permeability provided herein were obtained by using Worldwide Strategic Partners (WSP) Test Method 70.1.

Caliper

The caliper, or thickness, of a test specimen is measured as the distance between a reference platform on which the specimen rests and a pressure foot that exerts a specified amount of pressure onto the specimen over a specified amount of time. All measurements are performed in a laboratory maintained at 23° C.±2 C.° and 50%±2% relative humidity and test specimens are conditioned in this environment for at least 2 hours prior to testing.

Caliper is measured with a manually-operated micrometer equipped with a pressure foot capable of exerting a steady pressure of 0.50 kPa±0.01 kPa onto the test specimen. The manually-operated micrometer is a dead-weight type instrument with readings accurate to 0.01 mm. A suitable instrument is Mitutoyo Series 543 ID-C Digimatic, available from VWR International, or equivalent. The pressure foot is a flat ground circular movable face with a diameter that is smaller than the test specimen and capable of exerting the required pressure. A suitable pressure foot has a diameter of 25.4 mm, however a smaller or larger foot can be used depending on the size of the specimen being measured. The test specimen is supported by a horizontal flat reference platform that is larger than and parallel to the surface of the pressure foot. The system is calibrated and operated per the manufacturer's instructions.

Obtain a test specimen by removing it from an absorbent article, if necessary. When excising the test specimen from an absorbent article, use care to not impart any contamination or distortion to the test specimen layer during the process. The test specimen is obtained from an area free of folds or wrinkles, and it must be larger than the pressure foot.

To measure caliper, first zero the micrometer against the horizontal flat reference platform. Place the test specimen on the platform with the test location centered below the pressure foot. Gently lower the pressure foot with a descent rate of 3.0 mm±1.0 mm per second until the full pressure is exerted onto the test specimen. Wait 5 seconds and then record the caliper of the test specimen to the nearest 0.001 mm. In like fashion, repeat for a total of ten replicate test specimens. Calculate the arithmetic mean for all caliper measurements and report as Caliper to the nearest 0.001 mm.

Caliper Factor

The caliper factor, as mentioned previously is the caliper per 10 gsm of basis weight of the sample. So, the equation is caliper/(basis weight/10).

Density

Density is calculated based upon the basis weight and caliper with appropriate unit conversion to arrive at g/cc.

Material Compositional Analysis

The quantitative chemical composition of a test specimen comprising a mixture of fiber types is determined using ISO 1833-1. All measurements are performed in a laboratory maintained at 23° C.+2 C.° and 50%±2% relative humidity.

Analysis is performed on test samples taken from rolls or sheets of the raw material, or test samples obtained from a material layer removed from an absorbent article. When excising the material layer from an absorbent article, use care to not impart any contamination or distortion to the layer during the process. The excised layer should be free from residual adhesive. To ensure that all adhesive is removed, soak the layer in a suitable solvent that will dissolve the adhesive without adversely affecting the material itself. One such solvent is THF (tetrahydrofuran, CAS 109-99-9, for general use, available from any convenient source). After the solvent soak, the material layer is allowed to thoroughly air dry in such a way that prevents undue stretching or other deformation of the material. After the material has dried, a test specimen is obtained and tested as per ISO 1833-1 to quantitatively determine its chemical composition.

Compression Caliper

The caliper, or thickness, of a test specimen is measured as the distance between a reference platform on which the specimen rests and a pressure foot that exerts a specified amount of pressure onto the specimen over a specified amount of time. For this method, a series of pressures are applied to the test specimen for a specified time, with a recovery period in between. All measurements are performed in a laboratory maintained at 23° C.±2 C.° and 50%±2% relative humidity and test specimens are conditioned in this environment for at least 2 hours prior to testing.

Caliper is measured with a manually-operated micrometer equipped with a pressure foot capable of exerting a steady pressure onto the test specimen at each of the specified pressures (±0.01 kPa) in the stepped pressure series 0.50, 1.00, 2.00, 3.00, 5.00, and 0.50 kPa. The manually-operated micrometer is a dead-weight type instrument with readings accurate to 0.001 mm. A suitable instrument is Mitutoyo Series 543 ID-C Digimatic, available from VWR International, or equivalent. The pressure foot is a flat ground circular movable face with a diameter that is smaller than the test specimen and capable of exerting the required pressure. A suitable pressure foot has an area of 25 cm$^2$, however a smaller or larger foot can be used depending on the size of the specimen being measured. The test specimen is supported by a horizontal flat reference platform that is larger than and parallel to the surface of the pressure foot. The system is calibrated and operated per the manufacturer's instructions.

Obtain a test specimen from a sample of the material being evaluated. The test specimen is obtained from an area free of folds or wrinkles, and it must be larger than the pressure foot.

To measure caliper, first ensure the pressure to be exerted onto the sample is adjusted to the first pressure in the stepped pressure series, 0.50 kPa. Now zero the micrometer against the horizontal flat reference platform. Place the test specimen on the platform with the test location centered below the pressure foot. Gently lower the pressure foot with a descent rate of 3.0 mm±1.0 mm per second until the full pressure is exerted onto the test specimen. Wait 4 seconds, then record the caliper of the test specimen to the nearest 0.001 mm noting the test pressure applied. Remove the pressure from the test specimen and set a 30 second timer accurate to 0.1 seconds (any convenient source). Now adjust the pressure to the next pressure setting in the stepped series, 1.00 kPa, and zero the micrometer against the horizontal flat reference platform. After 30 seconds have elapsed, place the test specimen onto the platform with the same test location centered below the pressure foot. In like fashion, lower the pressure foot and record the caliper of the test specimen to the nearest 0.001 mm noting the pressure applied. Remove the pressure from the test specimen and set a 30 second timer. Repeat this entire process for each of the pressures in the stepped pressure series, in the order as follows: 0.50, 1.00, 2.00, 3.00, 5.00, 0.50 kPa. Record the caliper to the nearest 0.001 mm for each pressure, noting the pressure applied. For the 0.50 kPa pressure setting, note 0.50 kPa Initial and 0.50 kPa Final, respectively, along with the caliper. The caliper foot is to be applied to the same test location on the test specimen for each pressure applied.

In like fashion, repeat for a total of three replicate test specimens. Calculate the arithmetic mean for the caliper measurements at each pressure, and report as Caliper to the nearest 0.001 mm, noting the pressure applied for each, along with Initial and Final for the 0.50 kPa setting. From these results, Caliper Decrease can be calculated between any of the pressure settings used by simply subtracting the caliper obtained at a higher pressure from the caliper obtained at a lower pressure, and reporting to the nearest 0.001 mm.

Repetitive Acquisition Time and Rewet

Acquisition time is measured for an absorbent article dosed with Artificial Menstrual Fluid (AMF) as described herein, using a strikethrough plate and an electronic circuit interval timer. The time required for the absorbent article to acquire a series of doses of AMF is recorded. Subsequent to the acquisition test, a rewet test is performed. All measurements are performed in a laboratory maintained at 23° C.±2 C.° and 50%±2% relative humidity.

Referring to FIGS. 4-6B, the strikethrough plate 9001 is constructed of Plexiglas with an overall dimension of 10.2 cm long by 10.2 cm wide by 3.2 cm tall. A longitudinal channel 9007 that runs the length of the plate is 13 mm deep, 28 mm wide at the top plane of the plate, with lateral walls that slope downward at 65° to a 15 mm wide base. A central test fluid well 9009 is 26 mm long, 24 mm deep, 38 mm wide at the top plane of the plate with lateral walls that slope downward at 65° to a 15 mm wide base. At the base of the test fluid well 9009, there is an "H" shaped test fluid reservoir 9003 open to the bottom of the plate for the fluid to be introduced onto the underlying test sample. The test fluid reservoir 9003 has an overall length of 25 mm, width of 15 mm, and depth of 8 mm. The longitudinal legs of the reservoir are 4 mm wide and have rounded ends with a radius 9010 of 2 mm. The legs are 3.5 mm apart. The central strut has a radius 9011 of 3 mm and houses the opposing electrodes 6 mm apart. The lateral sides of the reservoir bow outward at a radius 9012 of 14 mm bounded by the overall width 2013 of 15 mm. Two wells 9002 (80.5 mm long×24.5 mm wide×25 mm deep) located outboard of the lateral channel, are filled with lead shot (or equivalent) to adjust the overall mass of the plate to provide a constraining pressure of 0.25 psi (17.6 g/cm$^2$) to the test area. Electrodes 9004 are embedded in the plate 9001, connecting the exterior banana jacks 9006 to the inside wall 9005 of the fluid reservoir 9003. A circuit interval timer is plugged into the jacks 9006, and monitors the impedance between the two electrodes 9004, and measures the time from introduction of the AMF into reservoir 9003 until the AMF drains from the reservoir. The timer has a resolution of 0.01 sec.

For the rewet portion of the test, the pressure applied to the test sample is 1.0 psi. The rewet weight is constructed such that the dimensions of the bottom face of the weight match the dimensions of the strikethrough plate, and the total mass required is calculated to give a pressure of 1.0 psi over the bottom face of the weight. Thus, the bottom face of the weight is 10.2 cm long by 10.2 cm wide, and constructed of a flat, smooth rigid material (e.g. stainless steel) to give a mass of 7.31 kg.

For each test sample, seven plies of filter paper cut to 150 mm diameter are used as the rewet substrate. The filter paper is conditioned at 23° C.±2 C.° and 50%±2% relative humidity for at least 2 hours prior to testing. A suitable filter paper has a basis weight of about 74 gsm, a thickness of about 157 microns with medium porosity, and is available from VWR International as grade 413.

Test samples are removed from all packaging using care not to press down or pull on the products while handling. No attempt is made to smooth out wrinkles. The test samples are conditioned at 23° C.±2 C.° and 50%±2% relative humidity for at least 2 hours prior to testing. Determine the dose location as follows. For symmetrical samples (i.e. the front of the sample is the same shape and size as the back of the sample when laterally divided along the midpoint of the longitudinal axis of the sample), the dose location is the intersection of the midpoints of the longitudinal axis and lateral axis of the sample. For asymmetrical samples (i.e. the front of the sample is not the same shape and size as the back of the sample when laterally divided along the midpoint of the longitudinal axis of the sample), the dose location is the intersection of the midpoint of the longitudinal axis of the sample and a lateral axis positioned at the midpoint of the sample's wings.

The required mass of the strikethrough plate must be calculated for the specific dimensions of the test sample such that a constraining pressure of 0.25 psi is applied. Measure and record the lateral width of the core at the dose location to the nearest 0.1 cm. The required mass of the strikethrough plate is calculated as the core width multiplied by the length of the strikethrough plate (10.2 cm) multiplied by 17.6 g/cm$^2$ and recorded to the nearest 0.1 g. Add lead shot (or equivalent) to the wells 9002 in the strikethrough plate to achieve the calculated mass.

Connect the electronic circuit interval timer to the strikethrough plate 9001 and zero the timer. Place the test sample onto a flat, horizontal surface with the body side facing up. Gently place the strikethrough plate 9001 onto the center of the test sample ensuring that the "H" shaped reservoir 9003 is centered over the predetermined dose location.

Using a mechanical pipette, accurately pipette 3.00 mL±0.05 mL of AMF into the test fluid reservoir 9003. The fluid is dispensed, without splashing, along the molded lip of the bottom of the reservoir 9003 within a period of 3 seconds or less. Immediately after the fluid has been acquired, record the acquisition time to the nearest 0.01 seconds and start a 5 minute timer. In like fashion, apply a second and third dose of AMF into the test fluid reservoir, with a 5 minute wait time between each dose. Record the acquisition times to the nearest 0.001 seconds. Immediately after the 3$^{rd}$ dose of AMF has been acquired, start a 5 minute timer and prepare the filter papers for the rewet portion of the test.

Obtain the mass of 7 plies of the filter paper and record as Dry Mass$_{fp}$ to the nearest 0.001 grams. When 5 minutes have elapsed after the third acquisition, gently remove the strikethrough plate from the test sample and set aside. Place the 7 plies of pre-weighed filter paper onto the test sample, centering the stack over the dosing location. Now place the rewet weight centered over the top of the filter papers and start a 15 second timer. As soon as 15 seconds have elapsed, gently remove the rewet weight and set aside. Obtain the mass of the 7 plies of filter paper and record as Wet Mass$_{fp}$ to the nearest 0.001 grams. Subtract the Dry Mass$_{fp}$ from the Wet Mass$_{fp}$ and report as Rewet Value to the nearest 0.001 grams. Thoroughly clean the electrodes 9004 and wipe off any residual test fluid from the bottom faces of the strikethrough plate and rewet weight prior to testing the next sample.

Immediately following the rewet portion of the test, proceed to the Stain Size method using the dosed test sample, as described herein.

In like fashion, repeat the entire procedure on ten replicate samples. The reported value is the arithmetic mean of the ten individual recorded measurements for Acquisition Times (first, second and third) to the nearest 0.001 seconds and Rewet Value to the nearest 0.001 grams.

Stain Size Measurement Method

This method describes how to measure the size of a fluid stain visible on an absorbent article. This procedure is performed on test samples immediately after they have been dosed with test liquid according to a separate method, as described herein (e.g. the Repetitive Acquisition and Rewet method). The resultant test samples are photographed under controlled conditions. Each photographic image is then analyzed using image analysis software to obtain measurements of the size of the resulting visible stain. All measurements are performed at constant temperature (23° C.±2 C.°) and relative humidity (50%±2%).

The test sample along with a calibrated ruler (traceable to NIST or equivalent) are laid horizontally flat on a matte black background inside a light box that provides stable uniform lighting evenly across the entire base of the light box. A suitable light box is the Sanoto MK50 (Sanoto, Guangdong, China), or equivalent, which provides an illumination of 5500 LUX at a color temperature of 5500K. A Digital Single-Lens Reflex (DSLR) camera with manual setting controls (e.g. a Nikon D40× available from Nikon Inc., Tokyo, Japan, or equivalent) is mounted directly above an opening in the top of the light box so that the entire article and ruler are visible within the camera's field of view.

Using a standard 18% gray card (e.g., Munsell 18% Reflectance (Gray) Neutral Patch/Kodak Gray Card R-27, available from X-Rite; Grand Rapids, MI, or equivalent) the camera's white balance is custom set for the lighting conditions inside the light box. The camera's manual settings are set so that the image is properly exposed such that there is no signal clipping in any of the color channels. Suitable settings might be an aperture setting of f/11, an ISO setting of 400, and a shutter speed setting of 1/400 sec. At a focal length of 35 mm the camera is mounted approximately 14 inches above the article. The image is properly focused, captured, and saved as a JPEG file. The resulting image must contain the entire test sample and distance scale at a minimum resolution of 15 pixels/mm.

To analyze the image, transfer it onto a computer running an image analysis software (a suitable software is MAT-LAB, available from The Mathworks, Inc, Natick, MA, or equivalent). The image resolution is calibrated using the calibrated distance scale in the image to determine the number of pixels per millimeter. The image is analyzed by manually drawing the region of interest (ROI) boundary around the visibly discernable perimeter of the stain created by the previously dosed test liquid. The area of the ROI is calculated and reported as the Overall Stain Area to the nearest 0.01 mm$^2$ along with notation as to which method was used to generate the test sample being analyzed (e.g. Repetitive Acquisition and Rewet).

This entire procedure is repeated on all of the replicate test samples generated from the dosing method(s). The reported value is the average of the individual recorded measurements for the Overall Stain Area to the nearest 0.01 mm$^2$ along with notation as to which method was used to generate the test samples that were analyzed (e.g. Repetitive Acquisition and Rewet).

Artificial Menstrual Fluid (AMF) Preparation

The Artificial Menstrual Fluid (AMF) is composed of a mixture of defibrinated sheep blood, a phosphate buffered saline solution and a mucous component. The AMF is prepared such that it has a viscosity between 7.15 to 8.65 centistokes at 23° C.

Viscosity of the AMF is performed using a low viscosity rotary viscometer (a suitable instrument is the Cannon LV-2020 Rotary Viscometer with UL adapter, Cannon Instrument Co., State College, PA, or equivalent). The appropriate size spindle for the viscosity range is selected, and instrument is operated and calibrated as per the manufacturer. Measurements are taken at 23° C.±1 C.° and at 60 rpm. Results are reported to the nearest 0.01 centistokes.

Reagents needed for the AMF preparation include: defibrinated sheep blood with a packed cell volume of 38% or greater (collected under sterile conditions, available from Cleveland Scientific, Inc., Bath, OH, or equivalent), gastric mucin with a viscosity target of 3-4 centistokes when prepared as a 2% aqueous solution (crude form, available from Sterilized American Laboratories, Inc., Omaha, NE, or equivalent), 10% v/v lactic acid aqueous solution, 10% w/v potassium hydroxide aqueous solution, sodium phosphate dibasic anhydrous (reagent grade), sodium chloride (reagent grade), sodium phosphate monobasic monohydrate (reagent grade) and deionized water, each available from VWR International or equivalent source.

The phosphate buffered saline solution consists of two individually prepared solutions (Solution A and Solution B). To prepare 1 L of Solution A, add 1.38±0.005 g of sodium phosphate monobasic monohydrate and 8.50±0.005 g of sodium chloride to a 1000 mL volumetric flask and add deionized water to volume. Mix thoroughly. To prepare 1 L of Solution B, add 1.42±0.005 g of sodium phosphate dibasic anhydrous and 8.50±0.005 g of sodium chloride to a 1000 mL volumetric flask and add deionized water to volume. Mix thoroughly. To prepare the phosphate buffered saline solution, add 450±10 mL of Solution B to a 1000 mL beaker and stir at low speed on a stir plate. Insert a calibrated pH probe (accurate to 0.1) into the beaker of Solution B and add enough Solution A, while stirring, to bring the pH to 7.2±0.1.

The mucous component is a mixture of the phosphate buffered saline solution, potassium hydroxide aqueous solution, gastric mucin and lactic acid aqueous solution. The amount of gastric mucin added to the mucous component directly affects the final viscosity of the prepared AMF. To determine the amount of gastric mucin needed to achieve AMF within the target viscosity range (7.15-8.65 centistokes at 23° C.) prepare 3 batches of AMF with varying amounts of gastric mucin in the mucous component, and then interpolate the exact amount needed from a concentration versus viscosity curve with a least squares linear fit through the three points. A successful range of gastric mucin is usually between 38 to 50 grams.

To prepare about 500 mL of the mucous component, add 460±10 mL of the previously prepared phosphate buffered saline solution and 7.5±0.5 mL of the 10% w/v potassium hydroxide aqueous solution to a 1000 mL heavy duty glass beaker. Place this beaker onto a stirring hot plate and while stirring, bring the temperature to 45° C.±5 C°. Weigh the pre-determined amount of gastric mucin (±0.50 g) and slowly sprinkle it, without clumping, into the previously prepared liquid that has been brought to 45° C. Cover the beaker and continue mixing. Over a period of 15 minutes bring the temperature of this mixture to above 50° C. but not to exceed 80° C. Continue heating with gentle stirring for 2.5 hours while maintaining this temperature range. After the 2.5 hours has elapsed, remove the beaker from the hot plate and cool to below 40° C. Next add 1.8±0.2 mL of the 10% v/v lactic acid aqueous solution and mix thoroughly. Autoclave the mucous component mixture at 121° C. for 15 minutes and allow 5 minutes for cool down. Remove the mixture of mucous component from the autoclave and stir until the temperature reaches 23° C.±1 C°.

Allow the temperature of the sheep blood and mucous component to come to 23° C.±1 C°. Using a 500 mL graduated cylinder, measure the volume of the entire batch of the previously prepared mucous component and add it to a 1200 mL beaker. Add an equal volume of sheep blood to the beaker and mix thoroughly. Using the viscosity method previously described, ensure the viscosity of the AMF is between 7.15-8.65 centistokes. If not the batch is disposed and another batch is made adjusting the mucous component as appropriate.

The qualified AMF should be refrigerated at 4° C. unless intended for immediate use. AMF may be stored in an air-tight container at 4° C. for up to 48 hours after preparation. Prior to testing, the AMF must be brought to 23° C.±1 C°. Any unused portion is discarded after testing is complete.

MD Bending Length

The measurements for MD Bending Length provided herein were obtained by using Worldwide Strategic Partners (WSP) Test Method 90.1.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A fluid management layer comprising an integrated, carded, nonwoven having a caliper of greater than 0.20 mm per 10 gsm for a basis weight of between about 40 grams per square meter (gsm) and about 75 gsm, the fluid management layer comprising a plurality of absorbent fibers, a plurality of stiffening fibers and a plurality of resilient fibers, as determined by the Material Compositional Analysis specified herein, the stiffening fibers comprising sheath-core bicomponent fibers having a core component comprising polyethylene terephthalate and a sheath component comprising polyethylene; wherein a plurality of heat-formed bonds are present between adjacent stiffening fibers; wherein the fluid management layer exhibits a total compression of greater than 0.40 mm and has a total recovery of at least 0.35 mm, as determined by the Compression Caliper method specified herein and wherein the fluid management layer has a density of less than or equal to 0.08 g/cc, as determined by the Density method specified herein.

2. The fluid management layer of claim 1, wherein the fluid management layer exhibits a total compression of between about 0.40 mm and about 0.70 mm.

3. The fluid management layer of claim 2, wherein the fluid management layer has a total recovery of at between about 0.35 and about 0.7 mm.

4. The fluid management layer of claim 1, wherein the fluid management layer exhibits a Caliper Decrease of at least about 0.13 mm, as a final caliper as measured at 1 kPa from 0.5 kPa, wherein Caliper Decrease is calculated as specified in the Compression Caliper method specified herein.

5. The fluid management layer of claim 4, wherein the fluid management layer exhibits a Caliper Decrease of between about 0.13 mm to about 0.30 mm, as a final caliper as measured at 1 kPa from 0.5 kPa.

6. The fluid management layer of claim 1, wherein the fluid management layer exhibits a Caliper Decrease of at least about 0.20 mm, as a final caliper as measured at 2 kPa from 0.5 kPa, wherein Caliper Decrease is calculated as specified in the Compression Caliper method specified herein.

7. The fluid management layer of claim 6, wherein the fluid management layer exhibits a Caliper Decrease of between about 0.20 mm and about 0.50 mm, as a final caliper as measured at 2 kPa from 0.5 kPa.

8. The fluid management layer of claim 1, wherein the fluid management layer exhibits a Caliper Decrease of at least about 0.25 mm, as a final caliper as measured at 2 kPa from 0.5 kPa, wherein Caliper Decrease is calculated as specified in the Compression Caliper method specified herein.

9. The fluid management layer of claim 8, wherein the fluid management layer exhibits a Caliper Decrease of between about 0.25 mm to about 0.60 mm, as a final caliper as measured at 3 kPa from 0.5 kPa.

10. The fluid management layer of claim 1, wherein the fluid management layer has a basis weight of between about 50 gsm to about 60 gsm, and wherein the nonwoven has density of from between 0.020 g/cc to 0.080 g/cc.

11. The fluid management layer of claim 10, wherein the fluid management layer has an air permeability of between about 200 m^3/m^2/min to about 400 m^3/m^2/min.

12. The fluid management layer of claim 1, wherein the fluid management layer exhibits a total compression of between about 0.41 and about 0.60 mm.

13. The fluid management layer of claim 1, wherein the fluid management layer exhibits a total compression of between about 0.43 and 0.55 mm.

14. The fluid management layer of claim 1, wherein the fluid management layer has a total recovery of at between about 0.36 mm and about 0.60 mm.

15. The fluid management layer of claim 1, wherein the fluid management layer exhibits a caliper decrease of between about 0.15 mm to about 0.25 mm, as a final caliper as measured at 1 kPa from 0.5 kPa.

16. The fluid management layer of claim 1, wherein the fluid management layer exhibits a caliper decrease of between about 0.30 mm to about 0.55 mm, as a final caliper measured at 3 kPa from 0.5 kPa.

17. A disposable absorbent article comprising a topsheet, a backsheet, an absorbent core disposed between the topsheet and the backsheet, and a fluid management layer of claim 1 disposed between the topsheet and the absorbent core.

18. The disposable absorbent article of claim 17, wherein the disposable absorbent article exhibits a stain size of less than less than 50 cm^2.

19. The disposable absorbent article of claim 18, wherein the disposable absorbent article exhibits a stain size of from between 30 cm^2 to about 50 cm^2.

20. The disposable absorbent article of claim 17, wherein the disposable absorbent article exhibits a stain size from between about 30 cm^2 to about 46 cm^2.

* * * * *